US007135615B2

(12) United States Patent
Kato

(10) Patent No.: US 7,135,615 B2
(45) Date of Patent: Nov. 14, 2006

(54) CHROMOSOME DOUBLING METHOD

(75) Inventor: Akio Kato, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 540 days.

(21) Appl. No.: 10/164,362

(22) Filed: Jun. 5, 2002

(65) Prior Publication Data

US 2003/0005479 A1    Jan. 2, 2003

Related U.S. Application Data

(60) Provisional application No. 60/296,183, filed on Jun. 5, 2001.

(51) Int. Cl.
*A01H 5/00* (2006.01)
*A01H 1/06* (2006.01)
(52) U.S. Cl. .................... 800/276; 800/320.1; 800/275
(58) Field of Classification Search ................ 800/260, 800/266, 269, 271, 275, 276, 278, 320.1, 800/299, 317.4; 435/468
See application file for complete search history.

(56) References Cited

FOREIGN PATENT DOCUMENTS

WO     WO 95/11967     5/1995

OTHER PUBLICATIONS

Eder et al. Theor. Appl. Genet. 104:703-708 (2002).*
Berdahl et al. Crop Sci. 31:1153-1155 (1991).*
Wright, Dissertation, Univ. Microfilms Int., Order No. DA831397 from Diss. Abstr. Int B, vol. 44, No. 4, 976, (1983).*
Dewey, Crop Sci. 17:106-111 (1977).*
Barnabas et al. Theor. Appl. Genet. 81:675-678 (1991).*
Kato, A. Maize Genet. Coop. Newsletter 71:36-37 (1997).*
Dvorak et al. Can. J. Genet. Cytol. 15:649-651 (1973).*
Katsiotis et al. J. Genet. & Breed. 48:415-421 (1994).*
Song et al. Euphytica 93:257-262 (1997).*
Meyerowitz. Cell 88:299-308 (1997).*
Montezuma-de-Carvalho. Euphytica 16:190-198 (1967).*
Kato. Biotechnic and Histochemistry 74(3):160-166 (1999).*
Ali et al. Genome 44:299-304 (2001).*
Ostergren. Genetica 27:54-64 (1954).*
Alemanno and Guiderdoni, "Increased doubled haploid plant regeneration from rice (*Oryza sativa* L. ) anthers cultured on colchicine-supplemented media," *Plant Cell Rep.*, 13:432-436, 1994.
Berdahl and Barker, "Characterization of autotetraploid Russian wildrye produced with nitrous oxide," *Crop Sci.*, 31:1153-1155, 1991.
Bordes et al., "Haplodiploidization of maize (*Zea mays* L.) through induced gynogenesis assisted by glossy markers and its use in breeding," *Agronomie*, 17:291-297, 1997.
Büter, "*In vitro* haploid production in maize," In: *In vitro haploid production in higher plants*, Jain, et al., Veilleux (eds.), Kluwer Academic Publishers, Dordrecht, The Netherlands, 37-71, 1997.

Chalyk, "Obtaining fertile pollen in maize maternal haploids," Maize Genet. Coop. Newslett. 74, 17-18, (www.agron.missouri.edu/mnl/74/93chalyk.html), 2000.
Chase, "Monoploids and monoploid-derivatives of maize (*Zea mays* L.)," *Bot. Rev.*, 35:117-167, 1969.
Coe, "A line of maize with high haploid frequency," *Am Nat*, 93(873):381-382, 1959.
Dvorak and Harvey, "Production of aneuploids in *Avena sativa* L. by nitrous oxide," *Can. J. Genet. Cytol.*, 15:649-651, 1973.
Dvorak et al., "The use of nitrous oxide for producing eupolyploids and aneuploids in wheat and barley," *Can. J. Genet. Cytol.*, 15:205-214, 1973.
Eder and Chalyk, "In vivo haploid induction in maize," *Theor. Appl. Genet.*, 104:703-708, 2002.
Gayen et al., "Chromosome doubling in haploids through colchicine," *Maize Genet. Coop. Newslett,.* 68:65, (www.agron.missouri.edu/mnl/68/101gayen.html), 1994.
Hansen and Andersen, "*In vitro* chromosome doubling with colchicine during microspore culture in wheat (*Triticum aestivum* L.)," *Euphytica*, 102:101-108, 1998.
Hansen et al., "Antimicrotubule herbicides for *in vitro* chromosome doubling in *Beta vulgaris* L. ovule culture," *Euphytica*, 101:231-237, 1998.
Hansen et al., "Nitrous oxide as a possible alternative agent for chromosome doubling of wheat haploids," *Plant Sci.*, 54:219-222, 1988.
Hansen et al., "Short-duration colchicine treatment for *in vitro* chromosome doubling during ovule culture of *Beta vulgaris* L.," *Plant Breeding,.* 114:515-519, 1995.
Jamieson et al., "An enzymatic method of preparing plant chromosomes for in situ hybridization," *Stain Technol.*, 61:21-25, 1986.
Kato, "Air drying method using nitrous oxide for chromosome counting in maize," *Biotechnic & Histochemistry*, 74(3):160-166, 1999.
Kato, "An improved method for chromosome counting in maize," *Biotech. Histochem.*, 72(5):249-252, 1997.
Kato, "Detection of an unfertilized polar nucleus with a fertilized egg cell," *Maize Genet Coop Newslett*, 66:105-106, 1992.
Kato, "Hematoxylin procedure for staining mature pollen grains in maize with dimethylsulfoxide as a clearing agent," *Biotech Histochem*, 73(1):1-5, 1998.
Kato, "Heterofertilization exhibited by trifluralin-induced bicellular pollen on diploid and tetraploid maize crosses," *Genome*, 44:1114-1121, 2001.
Kato, "Heterofertilization exhibited by using highly haploid inducing line "Stock 6" and supplementary cross," *Maize Genet Coop Newslett*, 64:109-110, 1990.

(Continued)

*Primary Examiner*—David T. Fox
*Assistant Examiner*—Keith O. Robinson
(74) *Attorney, Agent, or Firm*—Fulbright & Jaworski L.L.P.

(57)     ABSTRACT

The invention provides methods for chromosome doubling in plants. The technique overcomes the low yields of doubled progeny associated with the use of prior techniques for doubling chromosomes in plants such as grasses. The technique can be used in large scale applications and has been demonstrated to be highly effective in maize. Following treatment in accordance with the invention, plants remain amenable to self fertilization, thereby allowing the efficient isolation of doubled progeny plants.

44 Claims, 5 Drawing Sheets

OTHER PUBLICATIONS

Kato, "Induced single fertilization in maize," *Sex Plant Repord*, 10:96-100, 1997.

Kato, "Induction of bicellular pollen and dihaploidization of tetraploid maize," *Maize Genet Coop Newslett*, 70:25-26, 1996.

Kato, "Induction of bicellular pollen by trifluralin treatment and occurrence of triploids and aneuploids after fertilization in maize," *Genome*, 42:154-157, 1999.

Kato, "Nitrous oxide ($N_2O$) is effective for chromosome counting in maize," *Maize Genet Coop Newslett*, 72:32-33, 1998.

Kato, "Nitrous oxide ($N_2O$) is effective in chromosome doubling of maize seedlings," *Maize Genet. Coop. Newslett.*, 71:36-37 (www.agron.missouri.edu/mnl.html), 1997.

Kato, "Nitrous oxide—air drying method is effective for chromosome counting in maize," *Maize Genetics Conference Abstracts*, 40:24, ID # 145877, 1998.

Kato, "Single fertilization in maize," *Journal of Heredity*, 90:276-280, 1999.

Katsiotis et al., "Endosperm balance number and the polar-nuclei activation hypotheses for endosperm development in interspecific crosses of *Solanaceae* and *Gramineae*, respectively," *Theor. Appl. Genet.*, 91:848-855, 1995.

Montezuma-de-Carvalho, "The effect of $N_2O$ on pollen tube mitosis in styles and its potential significance for inducing haploidy in potato," *Euphytica*, 16:190-198, 1967.

Murata, "Staining air dried protoplasts for study of plant chromosomes," *Stain Technol.*, 58:101-106, 1983.

Östergren, "Colchicine mitosis, chromosome contraction, narcosis and protein chain folding," *Hereditas*, 30:429-467, 1944.

Östergren, "Polyploids and aneuploids of *Crepis capillaris* produced by treatment with nitrous oxide," *Genetica*, 27:54-64, 1954.

Pasakinskiene, "Culture of embryos and shoot tips for chromosome doubling in *Lolium perenne* and sterile hybrids between *Lolium* and *Festuca*," *Plant Breeding*, 119:185-187, 2000.

Petolino and Jones, "Anther culture of elite genotypes of maize," *Crop Sci.*, 26:1072-1074, 1986.

Petolino and Thompson, "Genetic analysis of anther culture response in maize," *Theor. Appl. Genet.*, 74:284-286, 1987.

Petolino et al., "Selection for increased anther culture response in maize," *Theor. Appl. Genet.*, 76:157-159, 1988.

Sallee, "Prefixation and staining of the somatic chromosomes of corn," In: *Maize for Biological Research*, Sheridan, (Ed.), University Press. University of North Dakota. p. 119, 1982.

Sarkar and Coe, "A genetic analysis of the origin of maternal haploids in maize," *Genetics*, 54:453-464, 1966.

Subrahmanyam and Kasha, "Chromosome doubling of barley haploids by nitrous oxide and colchicine treatment," *Can. J. Genet. Cytol.*, 17:573-583, 1975.

Taylor et al., Doubling the chromosome number of *Trifolium* species using nitrous oxide, *Crop Sci.*, 16:516-518, 1976.

Zeilinga and Schouten, "Polyploidy in garden tulips. II. The production of tetraploids," *Euphytica*, 17:303-310, 1968.

Various communications between the applicant and a third party.

Wright, "Doubled haploid production in barley (Hordeum Vulgare L.) using interspecific hybridization and nitrous oxide treatment," *Dissertation, Univ. Micrifilms Int.*, Order No. DA831397 from Diss. Abstr. Int B, vol. 44, No. 4, 976, 1983.

Kato, "Chromosome doubling of haploid maize seedlings using nitrous oxide gas at the flower primodial stage," *Plant Breeding*, 121:370-377, 2002.

\* cited by examiner

Chromosome doubling effects of nitrous oxide gas (6atm, 2days) on the maize haploid seedlings at various stages.

| Genotypes | Stage of the treatment | No. of doubled sectors/tassel | No. of anthers/tassel | Tassel branch No. | Tassel size (cm) | Plant height (cm) | Ear length (cm) | No. of doubled sectors / ear | No. of kernels / ear |
|---|---|---|---|---|---|---|---|---|---|
| B55 r | 4 leaf | 2.0 | 218 | 20.0 | 27 | 146 | 9.7 | 2.3 | 2.3 |
|  | 5 leaf | 2.2 | 67 | 13.4 | 28 | 167 | 11.8 | 1.4 | 42.2 |
|  | 6 leaf | 4.2 | 166 | 12.6 | 29 | 153 | 10.4 | 2.2 | 13.0 |
|  | 7 leaf | 6.0 | 169 | 13.4 | 29 | 156 | 11.8 | 2.6 | 95.2 |
|  | 8 leaf | 19.0 | 179 | 24.6 | 27 | 136 | 10.2 | 3.0 | 9.6 |
|  | cont | 0.0 | 0 | 32.0 | 33 | 165 | 11.5 | 1.5 | 1.5 |
| Oh43 r | 4 leaf | 0.0 | 0 | 4.3 | 18 | 109 | 10.3 | 0.5 | 0.5 |
|  | 5 leaf | 0.8 | 10 | 4.0 | 18 | 97 | 9.0 | 3.3 | 3.5 |
|  | 6 leaf | 0.8 | 6 | 5.8 | 13 | 103 | 10.8 | 1.8 | 24.0 |
|  | 7 leaf | 0.0 | 0 | 3.0 | 13 | 116 | 9.5 | 1.5 | 1.5 |
|  | 8 leaf | 1.0 | 1 | 5.0 | 13 | 115 | 9.0 | 1.0 | 1.0 |
|  | cont | 0.0 | 0 | 5.7 | 21 | 134 | 10.7 | 0.0 | 0.0 |

FIG. 4

CHROMOSOME DOUBLING METHOD

BACKGROUND OF THE INVENTION

This application claims the priority of U.S. Provisional Patent Application Ser. No. 60/296,183 filed Jun. 5, 2001, the disclosure of which is specifically incorporated herein in the entirety.

The government may own rights in this application pursuant to U S. Department of Energy grant number C-5-32680 DOE and the National Science Foundation grant number C-5-32942.

FIELD OF THE INVENTION

The present invention relates generally to the field of plant science and genetics. More specifically, it relates to improved methods for chromosome doubling in grasses.

DESCRIPTION OF RELATED ART

Several chemicals and physical treatments are known to induce chromosome doubling in plant cells. For example, colchicine, nitrous oxide gas, heat treatment, amiprophos methyl, trifluralin, oryzalin, and pronamide have been used to obtain progenies with doubled chromosome number in many plant species. Those chemicals and physical treatments are also used for chromosome counting because these treatments arrest mitosis and accumulates mitotic figures in the specimens. For example, colchicine (Jamieson et al., 1986; Murata, 1983; Sallee, 1982) and cold treatment (Rayburn and Gill, 1985) have been used for pretreatment to accumulate metaphase chromosome figures for chromosome observation in various plant species. 8-hydroxyquinoline (Aguiar-Perecin and Vosa, 1985; Carvalho and Saraiva, 1993; Chen, 1969; Jewell and Islam-Faridi, 1994; Lin, 1977; Rayburn and Gold, 1982; Sachan and Tanaka, 1977), monobromonaphthalene (Kindiger, 1994; Sallee and Kimber, 1981; Sallee, 1982), mixed solutions of monobromonaphthalene with colchicine (Hadlaczky et al., 1975), and colchicine with 8-hydroxyquinoline (Ward, 1980) were also used.

One application of chromosome doubling is the induction of pure lines by doubling the chromosome complement of haploids. There are many recent reports on chromosome doubling of seed propagating crops, e.g., rice (*Oryza saliva* L., Reiffers and Freire, 1990; Alemanno and Guiderdoni, 1994), wheat (*Triticum aestivum* L., Hansen and Andersen, 1998; Hassawi and Liang, 1991, Redha et al., 1998), oat (*Avena saliva* L. Kiviharju et al, 2000), and barley (*Hordeum vulgare* L., Furusho et al., 1999). Another use of chromosome doubling is to restore fertility to interspecific or intergeneric hybrids, e g., *Triticum* spp.x*Leymus* spp. (wheatxlymegrass, Anamthawat-Jonsson et al., 1997), *Avena strigosa* Schreb.x*Avena magna* Murphy et Terrell (Ladizinsky, 2000), *Lolium perenne* L.x*Festuca arundinacea* Schreb. (Pasakinskiene, 2000), and *Aegilops caudata* L.x*Triticum turgidum* L. (Simeone et al., 1989) Chromosome doubling is also used to overcome the crossing barrier between crops of different ploidies (Katsiotis et al., 1995).

Among treatments that have been used for chromosome doubling, colchicine has been extensively used to obtain progenies with doubled chromosome number in many plant species. Colchicine is very effective to obtain polyploids or doubled haploids in dicotyledonous species. However, in grass species, the chromosome doubling effects of colchicine are inconsistent. In grass species, the shoot meristem is more intensely surrounded by young leaves than dicotyledonous species. If colchicine is applied to the grass meristem, young leaves surrounding the shoot meristem are more heavily treated than the shoot meristem and the heavily treated leaves prevent the elongation of the shoot and result in the death of the shoot. After the death of the primary shoot, doubled sectors are sometimes observed in the secondary or tertiary branches at a low frequency. This process is laborious, unreliable and hazardous (Alemanno and Guiderdoni, 1994; Hansen et al., 1998; Pasakinskiene, 2000).

There are several reports that describe colchicine treatments on parthenogenetically induced haploid maize (*Zea mays* L.) seedlings (Bordes et al., 1997; Chalyk, 2000; Chase, 1952b, 1969; Eder and Chalyk, 2002; Gayen et al., 1994). Although haploid recovery rates of 26–41% were reported, colchicine treatments were affected by the growing conditions (Bordes et al., 1997), and the recovery rates could drop as low as 0.8–3.1%. It was observed that rapidly growing vigorous haploid seedlings were more prone to colchicine injury (Chase, 1969). Also, when colchicine or other anti-microtubule substances are applied as a liquid solution, the shoot meristem and surrounding tissue are injured. As a result, in maize, the flowering time of the tassel and the ear of treated plants will not be concordant, and self pollination becomes impossible. Further, penetration of colchicine into maize shoot meristem must be facilitated by vacuum, injection or submergence of the roots (Bordes et al., 1997; Chalyk, 2000; Chase, 1969; Eder and Chalyk, 2002; Gayen et al., 1994). Therefore, generally, colchicine treatments of shoots are tedious, hazardous and produce inconsistent results (Alemanno and Guiderdoni, 1994; Hansen et al., 1988, 1998; Pasakinskiene, 2000). For this reason, there has been no reliable method to obtain selfed progenies from haploid maize plants. Generally, treatment at seedling stages will cause considerable injury on other grass species and identification of appropriate treatment using colchicine is sometimes very difficult. For this reason chromosome doubling experiments in grasses have been less successful, particularly in maize.

Protocols for in vitro application of antimicrotubule agents were developed to overcome the low frequency of doubled sectors with shoot or seedling treatments (Wan et al., 1989, 1991; Hansen and Andersen, 1996, 1998; Hansen et al., 1995, 1998; Notsuka et al., 2000; Saisingtong et al., 1996; Wan et al., 1991). Several investigators have developed treatments of plant sections in vitro with colchicine or other anti-microtubule substances, e.g., trifluralin, oryzalin, amiprophos-methyl or pronamide. In these methods, dissected shoots, callus or microspores were treated with an antimicrotubule agent for a few days on a medium and plants with doubled chromosome numbers were consistently obtained. Both colchicine and amiprophos-methyl treatments proved to be effective for chromosome doubling of maize haploid calli, which were induced by anther culture. However, the application of these in vitro procedures for maize haploid breeding is rather difficult because most of the maize elite breeding lines will respond very poorly if at all to anther culture media (Byter, 1997; Petolino and Jones, 1986; Petolino and Thompson, 1987; Petolino et al., 1988). Also, in maize, male and female flowers emerge at different positions (e.g., a monoecious plant). Recent maize varieties produce only one shoot meristem.

In vitro chromosome doubling methods can not be applied for maize haploid seedlings induced by stock 6 (Coe ,1959; Sarkar and Coe, 1966), stock 6 derivatives (Bordes et al., 1997; Chalyk, 1994; Eder and Chalyk, 2002; Lashermes and Beckert, 1988, Sarkar et al., 1972) or stocks carrying ig gene (Kermicle, 1969, 1971; Kindiger and Hamann, 1993). This is because in each case the haploid embryos are obtained as dry kernels. Since these methods produce haploids at relatively high rates (0.5–8%), it is necessary to develop a reliable chromosome doubling method for haploid maize seedlings.

Another compound that has been shown to have an antimicrotubule effect and that has been used for chromosome doubling following colchicine is nitrous oxide gas ($N_2O$) (Stergren, 1944; 1954). The chromosome doubling effects of nitrous oxide gas were observed by Stergren (1944, 1954) and have been used to induce chromosome doubling in wheat (*Triticum dicoccum*, Khapli et al., 1960, Dvorak et al., 1973; ), wheat haploids (*Triticum aestivum* L; Hansen et al., 1988), barley (*Hordeum vulgare* L., Dvorak et al., 1973, Subrahmanyam and Kasha, 1975), red clover (*Trifolium pratense* L., Taylor et al., 1976), oat (*Avena sativa* L., Dvorak and Harvey, 1973), Russian wildrye (*Psathyrostachys juncea* (Fisch.) Nevski, Berdahl and Barker, 1991), potato (*Solanum tuberosum* L.; Montezuma-de-Carvalho, 1967) and tulip (*Tulipa* spp., Zeilinga and Schouten, 1968). $N_2O$ has been shown to induce partial chromosome doubling in maize shoot meristem and root tips (Kato, 1997a). Most of the prior investigations treated plants just after fertilization with 300–600 kPa nitrous oxide gas to prevent the first zygotic division in order to obtain progenies with doubled chromosome numbers. In maize, the prior methods entailed identifying haploids at the kernel stage.

Nitrous oxide gas, however, has often been considered to be less effective than colchicine for use with both grasses and dicotyledonous species, although some studies have suggested similar effects to colchicine (Hansen et al., 1988). Because the doubled cells induced by nitrous oxide gas tend to be outcompeted rapidly during growth. As a result, plants were treated just after fertilization to obtain progenies with doubled chromosome numbers. In this treatment the first cleavage of the fertilized egg cell is prevented by the gas and there is no elimination of doubled cells by competition. However, the occurrence of polyploids using this procedure is low. This has limited the applicability of chromosome doubling techniques in maize. In particular, this has limited the use of doubled haploids in maize plant breeding. There is, therefore, a great need in the art for novel methods of chromosome doubling in grasses and especially maize that can be used to obtain high yields of doubled progeny.

SUMMARY OF THE INVENTION

In one aspect, the invention provides a method of obtaining a plant with a doubled chromosome number. In certain embodiments of the invention, the method comprises the steps of: a) obtaining a starting plant, b) treating said plant with nitrous oxide gas during the stage, including the beginning of the stage, of development of said plant during which formation of the floral primordium (e.g., primordium of panicles, glumes, anthers, pistils, ovaries, tassels, ears) takes place (this includes the cell fate determination stage for differentiation of reproductive organs, even if there are no morphological changes at the growing points); c) self pollinating the plant; and d) selecting a progeny plant with doubled chromosome number derived from the self pollinating. In one embodiment of the invention, the starting plant may be further defined as a haploid plant wherein the progeny plant is a doubled haploid plant. The haploid plant may or may not be obtained from a hybrid plant, such an $F_1$ hybrid plant. The starting plant may also be an interspecific hybrid plant or intraspecific hybrid plant. In particular embodiments of the invention, the starting plant is heterozygous. Such a heterozygous plant may or may not be a member of a heterogeneous population of plants, such as from an open pollinated population of plants. The heterozygous plant may be from obtained from any heterozygous materials including local varieties, composites of different genetic backgrounds and other collections of plants.

In certain embodiments of the invention, plants are treated with a selected concentration (pressure) of nitrous oxide gas and oxygen (0.2 atm) or air (1 atm). The selected pressure of nitrous oxide gas may be at least 100 kPa, and may also be about 100 kPa to about 1400 kPa or even greater amounts of nitrous oxide, including about 100 kPa, 200 kPa, 300 kPa, 400 kPa, 500 kPa, 600 kPa, 700 kPa, 800 kPa, 900 kPa, 1000 kPa, 1100 kPa, 1200 kPa , 1300 kPa, and 1400 kPa. In further embodiments of the invention, plants are treated with nitrous oxide for a preselected period of time. The preselected period of time may be, for example, about 3 to about 24 hours. Alternatively, the preselected period of time may be about 24 to 72 hours, or longer, including about 24 hours to about 144 hours, such as about 24 hours, 36 hours, 48 hours, 60 hours, 72 hours, 96 hours, 120 hours and about 144 hours. The plants may be treated repeatedly.

The starting plant used with the invention may be a monocotyledonous plant. Examples of monocotyledonous plants include maize, rice, wheat, barley, oats, onion, rye, millet, sorghum, sugarcane, lily and turfgrass.

Self pollination of the starting plant can be done by any method, including natural self pollination and manual pollination. The starting plant can be haploid, diploid, triploid, tetraploid hexaploid, octoploid, or any higher level of ploidy that can be successfully doubled.

In another aspect of the invention, a method of plant breeding is provided. The method may comprise the steps of a) crossing at least a first and a second parent plant to produce a heterozygous plant comprising a selected genetic background, b) producing a haploid progeny plant derived from said hybrid plant, c) treating the haploid progeny plant with nitrous oxide gas during the stage of development of said progeny plant during which formation of the floral primordium; d) self pollinating the progeny plant; and e) selecting a doubled haploid progeny plant derived from the self pollinating, wherein the progeny plant has a desired genetic background It will be understood to those of skill in the art that floral primordium includes primordium of panicles, glumes, anthers, pistils, ovaries, tassels and ears and that the stage of development of the floral primordium includes the cell fate determination stage for differentiation of these reproductive organs, even there are no apparent morphological changes at the growing points.

In certain embodiments of the invention, the haploid plant is treated with a selected pressure of nitrous oxide gas. The selected pressure may be at least 100 kPa of nitrous oxide, and may also be about 100 kPa to about 1000 kPa or more of nitrous oxide, including about 100 kPa, 200 kPa, 300 kPa, 400 kPa, 500 kPa, 600 kPa, 700 kPa, 800 kPa, 900 kPa, 1000 kPa, 1100 kPa, 1200 kPa, 1300 kPa, and 1400 kPa. In further embodiments of the invention, the haploid plant is treated with nitrous oxide for a preselected period of time. In particular embodiments of the invention, the preselected period of time may be about 3 to about 24 hours. Alternatively, the preselected period of time may be at least 24 hours, including about 24 hours to about 144 hours, such as about 24 hours, 36 hours, 48 hours, 60 hours, 72 hours, 96 hours, 120 hours and about 144 hours.

In one embodiment of the invention the haploid plant is a monocotyledonous plant, such as a maize, rice, wheat, barley, oats, onion, rye, millet, sorghum, sugarcane, lily or turfgrass plant. Pollination of the plant can be by any method, including natural self pollination and manual pollination. The haploid plant may be derived from any plant and may be derived from a heterozygous plant. Such a heterozygous plant may or may not be a member of a heterogeneous population of plants, such as from an open pollinated population of plants. The heterozygous plant may be from obtained from any heterozygous materials including local varieties, composites of different genetic backgrounds and other collections of plants.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4: Shows results of $N_2O$ treatments of maize haploid seedlings from the inbred lines B55 and Oh43 at various stages of development. The 5–8 leaf stage (e.g., V3–V5 stage) corresponds to the flower primordia development stage. As can be seen, treatments at this stage were particularly efficacious in obtaining both doubled sectors and kernels per ear.

DESCRIPTION OF ILLUSTRATIVE EMBODIMENTS

Figure 1:
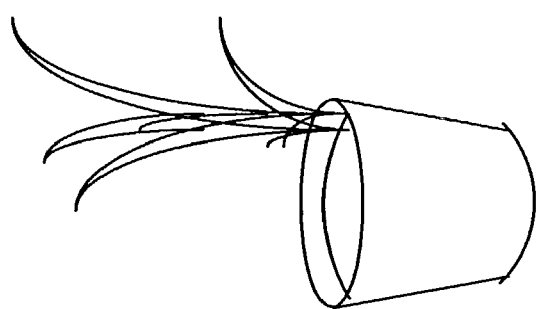
FIG. 1: Shows germinated seeds planted at the edge of a small pot filled with Promix or other soil in preparation for $N_2O$ treatment.

The invention overcomes the deficiencies of the prior art by providing a method for the efficient doubling of chromosomes. The technique has particular applicability to grass species. In particular, the invention provides a method of using $N_2O$ treatments that can be carried out during the flower primordia formation stage of development to obtain high yields of doubled sectors on reproductive organs in plants. The technique overcomes the low yields of doubled progeny associated with the use of prior techniques for doubling chromosomes in plants, particularly in grasses such as maize. Using the technique, plants may be treated for several days under pressure with $N_2O$.

The technique can be used in large scale applications and has been demonstrated to be highly effective in maize, for example, for the production of inbred lines by the chromosome doubling of haploid plants. This is because, following treatment with the technique, plants remain amenable to self pollination, thereby allowing the efficient isolation of doubled haploid progeny plants. Development of inbred lines is important because heterozygous plants do not breed true. Also, inbred lines are used for the production of hybrid varieties in crops that exhibit hybrid vigor, such as maize. These types of plants are generally grown by farmers as $F_1$ hybrids derived from the crossing of two parent inbred lines. Development of new inbred lines is thus crucial to the development of new crop varieties. Furthermore, doubling can be used to produce polyploid plants. Such polyploid plants may have improved agronomic traits and the development of a polyploid (for example, tetraploid) series in crops, vegetables and ornamental flowers (for example, lily) would provide superior varieties which can be used commercially.

Use of haploids to develop inbred maize lines has not been practically applied because of the inefficiency of chromosome doubling of maize haploid seedlings. The instant invention overcomes this difficulty by increasing the efficiency of chromosome doubling, allowing for the first time the practical application of the technique in breeding programs.

I. Chromosome Doubling

To overcome the shortcomings of prior chromosome doubling techniques, the inventor developed a technique for using nitrous oxide gas to induce doubled sectors on haploid plants. The technique results from studies carried out for the development of a high-yield technique for chromosome doubling in grasses and particularly, in maize. The new procedure induces doubled sectors on the flowers of grasses at a high rate (50–100%) without injuring seedlings. The results of nitrous oxide treatments are uniform and consistent. Carrying out the technique does not require special skills. With the technique, large number of plants (1000/day) can be treated by one person. In maize haploids, doubled sectors are induced both on the tassels and ears and self pollination is possible at 30–90% level, whereas no reliable procedure for chromosome doubling had previously been available.

Nitrous oxide is a gaseous substance that induces chromosome doubling in barley, red clover, rice and wheat. In an initial study using B55 haploids, it was observed that this gas, at 600 kPa of pressure, induced doubled sectors in both the tassel and the ear of the haploid plants. From these sectors, selfed progenies were obtained. In the treatment, maize plants were placed in a sealed iron chamber (8 inch diameter, 6 feet long), and treated with high pressure nitrous oxide gas at room temperature. Unlike with a liquid solution, precise control of the intensity and the duration of treatment was possible. Also, this procedure is good for treating many haploid plants at the same time uniformly. The plants were not damaged and sufficiently large numbers of doubled sectors were produced such that self pollination of haploids was possible.

Various $N_2O$ treatments can be used with the invention. For example, in one embodiment of the invention, treatment may comprise treatment with about 100 kPa, 200 kPa, 300 kPa, 400 kPa, 500 kPa and about 600 kPa of $N_2O$. Treatment may also, in other embodiment of the invention, include greater than 600 kPa of $N_2O$, for example, of about 700 kPa, 900 kPa, 1100 kPa, 1200 kPa, 1300 kPa, and 1400 kPa or greater amounts of $N_2O$. Treatment times may also vary in accordance with the invention, For example, treatment may be carried out for about 1 to about 3 days, including for 24, 36, 48, 60, and 72 hours. Treatment may also be less than 1 day, such as about 3, 6, 12 or 18 hours, or may be greater than 3 days, including about 4–6 days. A few to several treatments may be applied on the same plant at different growing stages. The six foot length treatment chamber has been made and used to treat haploid plants. It will be understood to those of skill in the art that the concentrations may be varied in accordance with parameters used. For example, it may be necessary to consider possible genotypic effects for the response to nitrous oxide gas. Further, treatment times will vary with temperature changes. For example, if the temperature is low, long treatments are possible; for instance, treatment can be 6 days in the case of treatment of lily bulbs.

Treatments at the 6 leaf stage were found to be best to induce fertile sectors on both tassels and ears in order to obtain selfed progenies. Unlike colchicine, nitrous oxide penetrates the plant tissue rapidly and uniformly. With nitrous oxide, a large number of seedlings can be treated (500–1000 seedlings) with consistent results by one person per day using multiple chambers, thus indicating the broad applicability of the procedure for plant breeding.

Optimization of the procedure may allow induction of more fertile anthers on haploids derived from Oh43 and A619. Multiple short treatments of haploid seedlings surrounding the 6 leaf stage may increase the number of fertile anthers and ovules. Multiple treatments may also improve fertile sector induction on the haploids of $F_1$s where the inbred parent lines have widely different maturities, since each haploid will have an assortment of alleles that may differentially affect ear and tassel development time. Spontaneous fungus attack during the treatment is another problem. Additional application of the fungicide mefenoxam, which has different anti-fungus activity from Captain, may be used to prevent fungus attack during the treatment.

II. Application of the Technique

One important application of the instant technique is in the breeding of crops. A particularly economically important crop for which the improvement of breeding methods is desirable is maize. Development of a reliable technique for haploid induction and chromosome doubling makes haploid breeding possible. Such a method can be utilized for rapid development of inbred lines, thereby contributing to the development of high performing varieties. The overall efficiency of haploid breeding is determined by both efficiencies of haploid induction and chromosome doubling.

1. Haploid Doubling for Breeding Crops

In crops (for example, maize, rice, wheat and barley) pure lines are utilized as varieties or the parents of varieties. Successive self pollinations (typically 6–10 generations) are necessary for the production of pure lines, and this can take several years. The doubling of haploids can be used to shorten the period of successive generations of self pollination that are typically required for development of new varieties of true-breeding lines. Because pure lines can be induced by doubling the chromosome number of haploids, utilization of haploids has been attempted in these crops from the middle of 20th century. In haploid breeding, both the haploid induction procedure and the doubling procedure are necessary. For haploid production in maize, the stock 6 line with the embryo-endosperm marker R1-scm2 enables the induction and rapid detection of haploids. What has been lacking is a suitable method for chromosome doubling of haploids in grasses, particularly maize. The instant invention provides such a method.

The goal of crop breeding is to combine various desirable traits in a single variety/hybrid. Standard breeding techniques take advantage of a plant's method of pollination. There are two general methods of pollination: a plant self-pollinates if pollen from one flower is transferred to the same or another flower of the same plant; a plant cross-pollinates if pollen comes to it from a flower on a different plant. Some plants, such as corn (*Zea mays* L.) have separate male and female flowers on the same plant, located on the tassel and the ear, respectively. Natural pollination occurs in corn when wind blows pollen from the tassels to the silks that protrude from the tops of the ear shoot. Manual pollination can also be carried out.

The development of a new plant hybrid variety generally involves two stages: (1) the selection of plants from various germplasm sources; and (2) the selfing of the selected plants for a number of generations to produce a series of inbred plants, which, although different from each other, each breed true and are highly uniform. Where the crop is grown as a hybrid, a third step is involved comprising (3) crossing selected inbred plants with unrelated inbred plants to produce hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. In the self pollinating crops, such as rice, wheat, barley etc. pure lines are directly utilized as commercial varieties. Thus the pure line development is important for commercial variety development in seed propagating crops and vegetables.

The selfing of plants to produce inbred lines typically involves five or more generations of selfing and selection to produce an inbred, e.g., $F_1 \rightarrow S_1$; $S_1 \rightarrow S_2$; $S_2 \rightarrow S_3$; $S_3 \rightarrow S_4$; $S_4 \rightarrow S_5$; $S_5 \rightarrow S_6$ etc. After at least six generations, the inbred plant is typically considered genetically pure and will breed true to type. Thus, plants that have been self-pollinated and selected for type over many generations become homozygous at almost all gene loci and produce a uniform population of true breeding progeny, e.g., a homozygous plant. A cross between two such homozygous plants produces a uniform population of hybrid plants that are heterozygous for each gene locus. Conversely, a cross of two plants each heterozygous at a number of loci produces a population of hybrid plants that differ genetically from each other and are not uniform. The resulting non-uniformity makes performance of the hybrid unpredictable.

The problem with the technique of repeated inbreeding is that it is time and labor intensive. Breeding five generations may take several years and may require significant labor and selection of progeny. Chromosome doubling of haploids represents a useful way of shortening this process by providing another way of making inbred lines. Through preparation of a haploid from a diploid heterozygous plant followed by the doubling of the haploid, a diploid plant is produced which is homozygous at each locus. The method is advantageous because of its relatively short period of development. In rice, wheat and potato, haploids have been used for breeding. In maize, however, haploids have not been employed because, using prior techniques, of the difficulty in self pollinating haploid plants that have small doubled sectors in separate male and female flowers. The instant invention allows the efficient use self-pollinations, however. This allows elimination of the repeated self fertilizations. Thus, a heterozygous plant at any generation (e.g., $F_1-S_4$) can be used as materials for the preparation of a doubled haploid.

Using the haploid doubling procedure for plant breeding, the initial stage of plant breeding is generally the same as that using standard techniques. For example, breeding is initially used to combine the genetic backgrounds from two or more starting plants or various other broad-based sources into breeding pools from which new inbred plants are developed by haploid breeding. One technique for combining desired genetic backgrounds is pedigree breeding. The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses can be selfed and selected in successive generations. At any succeeding generation, preferably when the desired genetic backgrounds have been combined, doubled haploids can be produced to make true-breeding lines. These lines may then be subject for performance analyses and either eliminated or maintained based on the characteristics of the variety developed.

In selecting a second parental inbred line to cross for development of a new hybrid variety, it will typically be desired to choose plants which either themselves exhibit one or more selected desirable characteristics or which exhibit the desired characteristic(s) when in hybrid combination. Corn plants (Zea mays L.) can be crossed by either natural or mechanical techniques. Natural pollination occurs in corn when wind blows pollen from the tassels to the silks that protrude from the tops of the recipient ears. Mechanical pollination can be effected either by controlling the types of pollen that can blow onto the silks or by pollinating by hand.

2. Exemplary Process for Producing Doubled Haploids

Haploid kernels can be induced by pollinating colorless aleurone plants (inbred or hybrid) with the pollen of Stock 6 homozygous for the R1-scm2 gene and other color factors. This allele of r1 conditions color in the embryo as well as the aleurone. Ninety four percent of kernels identified by this method were haploid. In comparison, R1-nj, another embryo color marker gene commonly used for haploid kernel identification (Greenblatt and Bock, 1967), could result in a misclassification rate 80% (Nanda and Chase, 1966). Because the C1-I allele is very infrequent among the U.S. dent breeding lines, the R1-scm2 color marker is used effectively to distinguish haploid kernels at the dormant stage.

Kernels with a haploid embryo that exhibit colored aleurone and colorless scutellum (0.5–2%) may then be separated. Among the kernels with colored aleurone and colorless scutellum, diploids and aneuploids are occasionally observed (5%). However, those non-haploids can be distinguished by their higher plant height and high fertility Kernels on the ears are dissected and if necessary germinated for chromosome counting using root tips. Chromosome number determination may be conducted using the $N_2O$ gas method (Kato, 1999a), or the method utilizing heat pretreatment (Kato, 1997b). By this method determination of chromosome numbers of 50 samples per day is possible.

The haploid seedlings can then be doubled using the invention, for example, by treating the plant with pressurized $N_2O$ gas for 1–3 days (600–800 kPa) at the time of flower primordia formation (4–7 leaf stage, at this stage 4–7 leaves are fully excluded from the leaf whole). At the 4 leaf stage, four elongated leaves are observable, and the tip of fifth leaf is appear at the leaf whorl (stage V3 according to Ritchie et al., 1997). At the 5 leaf stage, five elongated leaves, are observable, and the tip of sixth leaf is appear at the leaf whorl (stage V4). At the 6 leaf stage, six elongated leaves are observable, and the tip of seventh leaf is appear at the leaf whorl (stage late V4 or early V5). At the 7 leaf stage, seven elongated leaves are observable, and the tip of eighth leaf is appear at the leaf whorl (middle stage V5).

Doubled sectors can be detected on tassels with fertile anthers, while in the non-doubled sector, anthers do not protrude or the rarely protruded anthers are shriveled and sterile. On a pollinated ear, doubled sectors can be detected as plump kernels. Care is necessary to determine the $N_2O$ effect from spontaneous chromosome doubling. Evaluation of the doubling effects in flowering organs can be made rapidly with the naked eye.

3. Chromosome Doubling in Interspecific Hybrids in Grasses

In some crops (for example, wheat and tallfescue) interspecific hybrids are utilized as varieties. Generally those interspecific hybrids are highly sterile. However, if the chromosome numbers are doubled they restore fertility. The invention thus also has applicability for the doubling of chromosome number of interspecific hybrids, thereby potentially restoring fertility of the interspecific hybrids. In some combinations of rice intraspecific crosses, the hybrids show sterility. For example, indica×japonica crosses exhibit high sterility because of their distant genetic relationships. This technique may be used to restore fertility in the crosses.

4. Production of Polyploids

The development of an efficient chromosome doubling combined with a haploid induction method also makes it possible to construct a ploidy series (n, 2n, 3n, 4n, 6n, 8n) of any given inbred line. Dosage effects in maize have been investigated utilizing B-A translocations (Birchler, 1991; 1994c), aneuploids (Guo and Birchler, 1994) and the el mutation (Guo et al., 1996). Establishing ploidy series of inbred lines will contribute to the research advances in this field. Those polyploids can be used as one of parent of interspecific crosses to overcome ploidy barriers between crop species.

Induction of tetraploids from diploids is more difficult than obtaining diploids from haploids in maize. Successful chromosome doubling of diploids has been reported using heat treatment just after fertilization (Randolph, 1932), the el mutation (Alexander, 1957; Rhoades and Dempsey, 1966), or colchicine treatment of seedlings (Guenov, 1991). Among these methods, the el gene is frequently used (Birchler, 1994b), because the heat treatment of developing ovules and the colchicine treatment of seedlings are difficult to repeat. The induction of tetraploids in known inbred lines is difficult because successive back crossing is necessary if the el gene is to be used to obtain tetraploids. Consequently there are only two tetraploid inbred lines from diploid inbred lines (N6, W23) registered in the Maize Stock Center (in Maize Genetics Cooperation Newsletter, 1997, pp117.). Therefore, the chromosome doubling method using nitrous oxide on diploid seedlings—will enable construction of tetraploid inbred series from elite maize inbred lines, representing a significant advance.

5. Species for Application of the Technique

The current invention could potentially be used with any plant species which is susceptible to the mitotic or meiotic disrupting effects of $N_2O$ during formation of the floral primordia. However, the invention will find particular use in those species for which prior techniques have found limited utility in chromosome doubling, and particularly in grasses, including maize. Examples of species deemed especially useful with the invention include, but are not limited to, maize (Zea mays L.), rice (Oryza sativa L.), common wheat (Triticum aestivum L.), durum wheat, barley, oat, rye, sorghum (Sorghum bicolor L.), onion (Allium cepa L.), Jobstears (Coix lacryma-jobi L.), millet, sugarcane, lily and tallfescue (Festuca arundinacea Schreb.), Italian rye grass and any kind of turfgrass or forage grasses.

III. Preparation of Haploids

Haploid plants in maize have been induced by various methods (e.g., 0.1–3%), but low frequencies (5%) of doubled sectors on the tassels have limited the feasibility of the technique. Three methods are currently available for obtaining haploids in maize: pollination by stock 6, utilization of the indeterminate gametophyte gene and anther culture. Among these techniques, the stock 6 method is the most reliable procedure to induce haploids in diverse lines (the occurrence of haploids is 0.5–2%). Kernels with haploid embryos can be identified using an embryo anthocyanin pigment marker.

Induction of haploids is important in plant breeding, because it allows the development of pure lines in a short period by successive chromosome doubling and selfing. In maize, where inbred lines (pure lines) are used for the development of hybrid varieties, utilization of haploids was proposed nearly fifty years ago (Chase, 1952). However, the difficulties of obtaining a large number of haploids and of chromosome doubling of induced haploids prevented doubled haploids from being widely utilized for breeding. In other crops, for example, rice, tobacco, potato, and wheat, haploid breeding is conducted to some extent. The three general methods to induce haploids in maize are described below.

1. Anther Culture

Successful anther culture of maize was first reported in China (Anonymous, 1975; reviewed by Wan and Widholm, 1993), and the method to improve the response from anther culture was investigated further (Barloy et al., 1989; Dieu and Beckert, 1986; Genovesi and Collins, 1982; Mitchell and Murigneux et al., 1993; Petolino et al., 1988; Petolino 1991; Petolino and Thompson 1987). Methods to induce chromosome doubling in anther culture have been investigated using colchicine and antimicrotubule herbicides (Saisingtong et al., 1996; Wan et al., 1989; 1991), and many doubled haploid lines from regenerated plants have been established (Murigneux et al., 1993). Improvement of anther culture response was accomplished by crossing regenerated plants with each other (Petolino et al., 1988). Anther culture is very productive to induce haploids in particular lines. The problem is that many maize elite inbred lines do not respond or very poorly respond to the anther culture media, and the procedure is rather cumbersome as a breeding technique. Also, in maize, during the regeneration process, the plants tend to exhibit abnormal growth (tassel seed, or female sterility) so selfing is often difficult. Because of these features, anther culture is not readily applicable to maize breeding.

2. Parthenogenesis

Parthenogenesis is a phenomenon where an unfertilized egg develops into a haploid embryo. Normal maize plants produce parthenogenetic haploids in progenies at a frequency of 0.1% (Chase, 1949). Historically, the first maize haploids were obtained through parthenogenesis and in the early days of maize research, spontaneous haploids resulting from parthenogenesis were the only source (reviewed by Chase, 1969). Subsequently, the embryo-endosperm marker, R1-nj, was introduced, w normal kernels (Greenblatt and Bock, 1967; Nanda and Chase, 1966). In this system, R1-nj conditions purple pigmentation in both the aleurone layer and scutellum; therefore kernels with haploid embryos exhibit colored aleurones with colorless embryos when R1-nj is used as a male parent onto the recessive r1.

A high haploid inducing line, Stock 6, was discovered by Coe (1959), with an incidence of parthenogenesis of 2.5–3.0% in selfed progenies and 0.5–2.0% when the pollen is crossed to other stocks (Coe and Sarkar, 1964). While both male and female effects were detected, the pollen has the primary role to induce haploids and the trait is heritable (Sarkar and Coe, 1966). Efforts to increase the haploid-inducing ability have been made and a few highly-haploid-inducing lines have been developed (Aman and Sarkar, 1978; Chalik, 1994; Lashermes and Beckert, 1988; Sarkar et al., 1972). The problems with these methods were low haploid incidence (1–5%), and difficulty with inducing chromosome doubling on haploid seedlings.

The results presented below demonstrate the effectiveness of identifying haploid kernels at the dormant stage using the R1-scm2 color marker. This allele of r1 conditions color in the embryo as well as the aleurone. Ninety four percent of kernels identified by this method were haploid. In comparison, R1-nj, another embryo color marker gene commonly used for haploid kernel identification (Greenblatt and Bock 1967), could result in a misclassification rate 80% (Nanda and Chase1966). Because the C1-I allele is very infrequent among the US dent breeding lines, the R1-scm2 color marker is used effectively to distinguish haploid kernels at the dormant stage.

3. Indeterminate Gametophyte

In maize, a very rare phenomenon exists wherein a sperm cell enters an ovule and develops into a haploid embryo. The phenomenon is called androgenesis, and the frequency is only 1/80,000 in normal lines (Goodsell, 1961). The gene called indeterminate gametophyte (ig), discovered by Kermicle (1969; 1971), induces a high frequency of androgenesis. The stock with the ig mutation bears androgenic haploids at a frequency of 0.1–1%. Both heterozygous and homozygous ig produce haploids because ig works gametophytically. The irregular structure of the female gametophyte induces several pleiotropic effects including the occurrence of androgenesis (Lin, 1978). This method is utilized to introduce cytoplasmic male sterility into inbreds by backcrossing (Kindiger and Hamann, 1993). This may provide a haploid frequency up to 8%.

4. Summary

Among these three procedures, parthenogenesis using a haploid inducing line is considered to be most useful in breeding programs, where vast number of lines and progenies have to be evaluated every year. The difficulty of chromosome doubling which had prevented the widespread use of parthenogenesis is solved by the current invention. However, the low frequency of haploid inducing frequency is still the problem for wide application of parthenogenesis for haploid breeding. Further improvement of haploid induction frequency are needed.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Breeding System for Production of Doubled Maize Haploid Inbred Lines

The invention provides a system for inducing doubled sectors on flowers of grasses to obtain progenies with doubled chromosome number. The system is useful, for example, to obtain diploid plants from haploids at a high frequency in grasses. In maize haploids, self pollination becomes possible using this system. An exemplary procedure for doubling maize haploids that was used to produce doubled haploid plants is described below.

Maize haploids were induced by the stock 6 procedure (Coe 1959) and separated by the color marker R1-scm2 (Kato, 1999c). The procedure was demonstrated using haploids produced for the maize inbred lines B55 (Iowa Agric & Home Econ Exp Stn., Iowa) and Oh43 (Ohio Agric Res & Dev Ctr, Ohio, 1949). Haploid seeds were surface sterilized with the fungicide Captan and germinated in moist vermiculite at 30° C. for two days. The germinated seeds were planted at the edge of a small pot filled with ProMix (FIG. 1).

Figure 2:
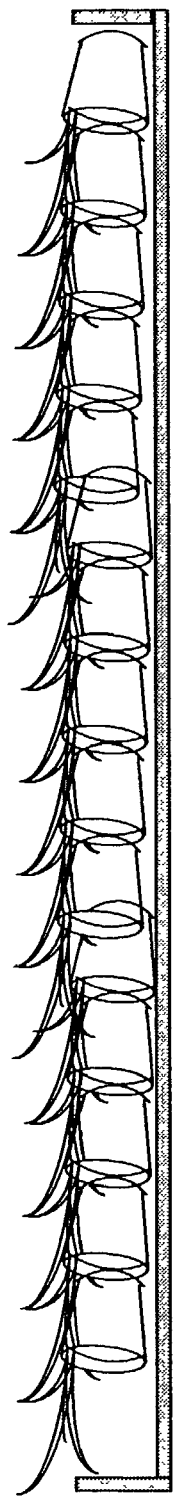
FIG. 2: Seedlings are placed horizontally in a cartridge made of cardboard or a plastic case for placement in the $N_2O$ treatment chamber.
Figure 3:
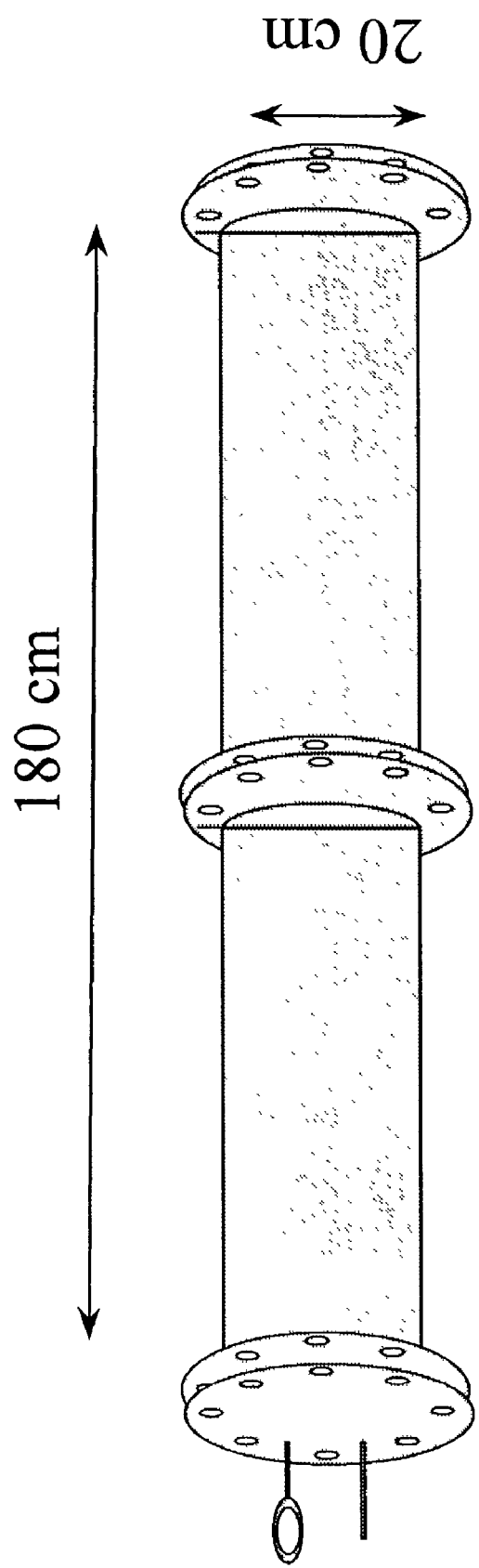
FIG. 3: Shows chamber for $N_2O$ treatment of plants.
Figure 5:
FIG. 5: Shows cross section of maize seedling during floral primordia formation (Kiesselbach, 1949).
Figure 6:
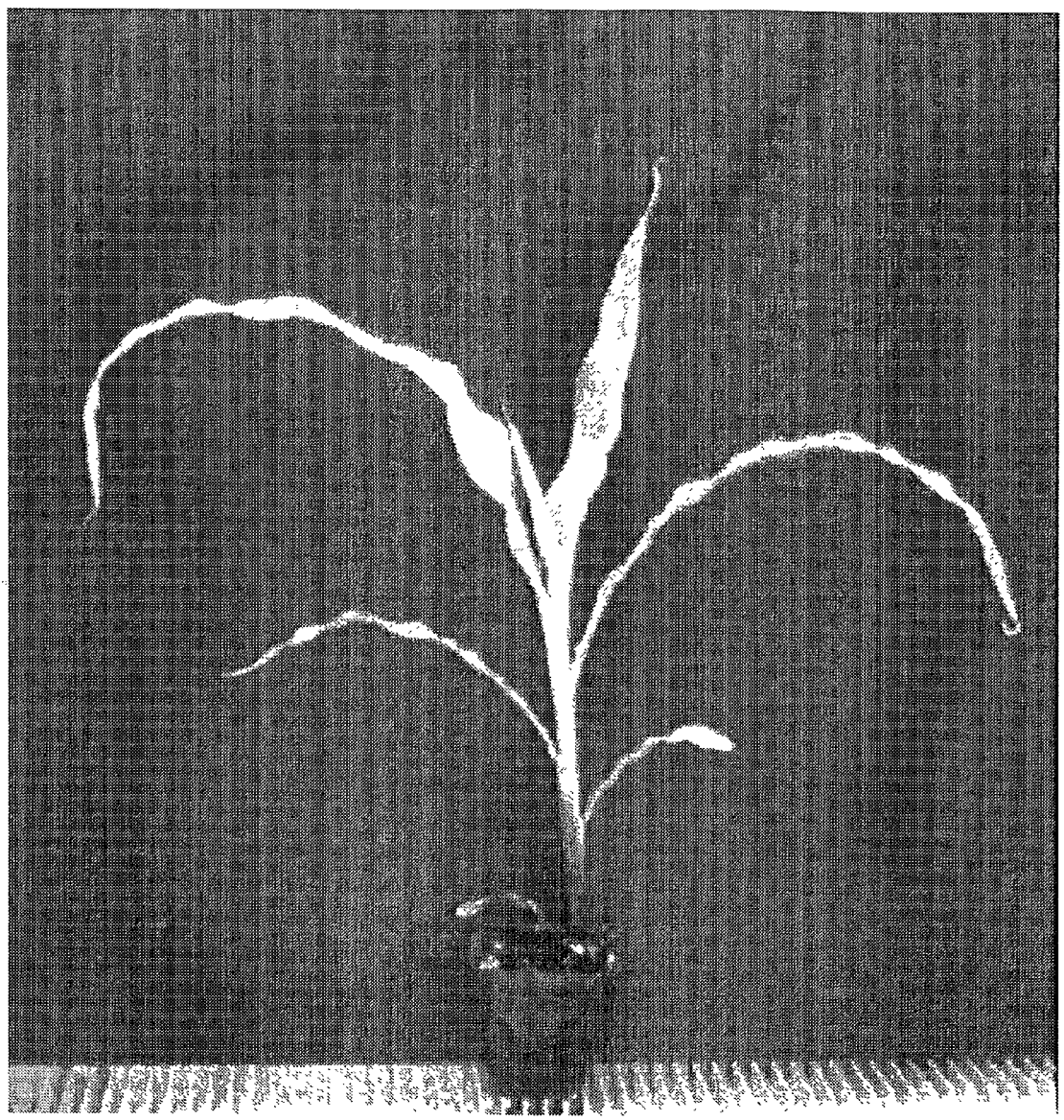
FIG. 6: Maize plant shown during 6 leaf stage.

The seedlings were treated at various stages from the 4 leaf to 8 leaf stage with nitrous oxide gas as described below. Prior to treatment, the seedlings were placed horizontally in a cartridge made of cardboard or, more preferably, a plastic carpet (FIG. 2). Application of a water mist to the plastic carpet may be used to prevent the occurrence of a static charge. Then the cartridge was introduced into a nitrous oxide chamber (20 cm in diameter and 180 cm in length with silicone rubber packing) (FIG. 3). The chamber was made from steel pipes and flanges designed for industrial use. Two 3 foot long pipes with flanges at both sides were connected to each other with 8 bolts to form the chamber. Iron covers were applied at the both ends. One end cover had a valve and a pressure gage. The chamber was preferably earthed.

The chamber was filled with nitrous oxide gas at the pressure of 6 atm (600 kPa ) for two days at room temperature. Application of a fungicide solution on the soil (e.g., Captan) was preferable before treatment to prevent possible fungus attack on roots. Survival rate could be increased by application of the fungicides Metalaxyl or Mefenoxam combined with Captan. A lesser amount of moisture in the soil was found to be preferable at this time to avoid root injury. Because the gas from the tank was very cold, use of a long introductory tube (5 m) submerged in water was made to warm up the gas before introduction into the chamber. Application of paper wrapped moistened calcium hydroxide was also preferable to absorb accumulating carbon dioxide in the chamber. The maize plants survived rapid air pressure change.

After $N_2O$ treatment the seedlings were kept at warm temperature (20–25° C.) in the greenhouse for two to three days and transplanted to the field or pots in the greenhouse. Most of treated plants will recover without special care. But some treated plants (10%) were sensitive to drought following treatment, thus they were shaded or covered with a polyethylene bag if necessary upon transplantation. The plants were then grown and self pollinated. Cultivation and self pollination methods were the same as for diploid maize plants. However, where possible, growing plants in a greenhouse was found to be preferable to obtain maximum harvest. The results of the analysis are given in FIG. 4. As can be seen, treatment at the 5–7 leaf stage (e.g., the flower primordium formation stage), was found to provide the greatest number of both doubled sectors and kernels per ear. Using the technique, 70–90% of B55 haploid plants could be self pollinated. This represents a significant advance over the previously used colchicine treatments, which yielded an estimated selfing rate of between 5–15%.

Example 2

Procedure for Haploid Induction

Kernels with haploid embryos were induced using the maize line stock 6 (Coe 1959). Pollen of stock 6 has the ability to induce haploids (Sarkar and Coe 1966) on the ears of diverse maize lines at a frequency (0.5–3%). Four inbred lines (A619, B55, B73, and Oh43 ) and four hybrids (B55×A619, B73 R1-scm2×A619 R1-scm2, Oh43×Mol7, and W22×W23) were used as seed parents. B73 was included because this line shows a high frequency of spontaneous chromosome doubling. After detasseling, the ears of the seed parents were pollinated by stock 6 R1-scm2, bz2 (made by successive back crossing of stock 6 to a line carrying R1-scm2, bz2, that was obtained from the Maize Genetics Cooperation Stock Center, Urbana Ill. U.S.A., //www.aces uiuc.edu/maize-coop/). The R1-scm2 gene induces deep purple pigmentation in both the aleurone layer of the endosperm and the scutellum of the embryo (Kato, 1999b; Kermicle, 1971; Robertson, 1984). Haploid kernels were detected as having colorless scutella and purple aleurone. A portion of pericarp over the scutellum was peeled to facilitate the determination if necessary. For the hybrid B73 R1-scm2×A619 R1-scm2, the pollen of stock6 C1-I was used. The gene, (C1-I, is a dominant anthocyanin color inhibitor. In this case, haploid kernels were detected as having colorless aleurone and colored embryos (Coe and Sarkar 1964).

About 30–100 ears were pollinated to produce 50–200 haploid kernels of each line. In the haploid detection system using stock 6, R1-scm2, as a pollinator, a small portion (5.7%) of identified kernels were hypoploids, diploid hybrids, or spontaneous doubled haploids. Those haploids and non-haploids were identified using the following criteria:

Haploids—narrow leaves, white stripes in the leaves, short plant height, high sterility in both tassel and ear. Occasional sectorial restoration of fertility on the tassel and ear (Chase 1969).

Hybrids—presence of hybrid vigor, high fertility of both tassels and ears, absence of sectorial sterility, segregation of purple aleurone color (R1-scm2 and r1), and yellow and white endosperm (Y1 from seed parents and y1 from stock 6) on the selfed ears.

Hypoploids—high fertility of tassel, absence of sectorial sterility or fertility, semisterile condition of the selfed ear, and segregation of yellow and white endosperm (y1, from stock 6) on the selfed ears.

Spontaneous doubled haploid—high fertility of both tassels and ears, lack of hybrid vigor, no segregation of kernel type.

The haploid kernels were treated with the fungicide Captan and germinated in moist vermiculite at 30 $_t$C. The germinated seeds were transferred to small plastic pots filled with ProMix, a peat moss based growing medium (Hummert, St. Louis, Miss.). The seedlings were grown in a greenhouse for one to four weeks. Stock 6 induced 1–5 putative haploid kernels per ear (purple kernel with white embryo or yellow kernel with purple embryo) on all genotypes. A total of 715 putative haploid kernels were planted for the experiments. Most of them (94%) were determined to be haploid from their morphology and high sterility. The remaining 4.7% were misclassified $F_1$s, 1.1% were hypoploids, and 0.3% (one plant induced from B73 and one plant from Oh43×Mol7) were spontaneous doubled haploids. Among 623 haploids used in the experiments, 450 haploid seedlings were treated with nitrous oxide gas; 92% survived the treatment. In a second study, fourteen out of 50 treated Oh43 haploid seedlings died from fungus attack.

Example 3

Determination of the Optimal Treatment Stage to Induce Fertile Sectors on Haploids Haploid seedlings induced from inbred lines Oh43 and B55 were treated with nitrous oxide gas (600 kPa+100 kPa air, 2 days, room temperature) at the 3, 4, 5, 6, 7, or 8 leaf stage. Leaf stages were defined as follows, At the 3 leaf stage, there are three elongated leaves and the tip of the fourth leaf appears at the center of the leaf whorl. This stage is defined as V2 according to Ritchie et al. (1997). At the 8 leaf stage, there are 8 elongated leaves and the tip of the 9th and 10th leaves appear at the center of the leaf whorl (late V5 stage). At the 6 leaf stage, six elongated leaves are observable, and the tip of seventh leaf appears at the leaf whorl (late V4 or early V5 stage). Nine to sixteen haploid plants were treated at each stage using a large air tight iron chamber (FIG. 3). Up to fifty seedlings can be contained and treated with nitrous oxide gas in this size of chamber (20 cm inner diameter, 180 cm in length, with silicone rubber packing). Moistened calcium hydroxide (50 g) wrapped in a paper towel was included to absorb carbon dioxide that is produced by the seedlings, as carbon dioxide at high concentration will injure the seedlings during the treatment. The soil of the pots was dried prior to treatment to prevent root injuries. Because nitrous oxide gas is very cold when it is released from the tank, a water submerged plastic pipe (5 m) was used to warm the gas. The gas was introduced slowly into the chamber over a 10 minutes time frame.

After the treatment, seedlings were transplanted into larger pots, and grown in a greenhouse. A relatively cool temperature (below 25° C.) was maintained to permit the appropriate development of doubled sectors. At flowering, the ears were cross pollinated by an appropriate pollen source to reveal all the fertile sectors on the ears. On the treated plants, plant height (cm), tassel size (cm), number of tassel branches, ear length (cm), the number of fertile sectors on a tassel and an ear, the number of anthers on a tassel, and the number of kernels on an ear were recorded.

Analyses of variance and Duncan's Multiple Range Tests were performed to determine the effects of treatments on the plant height (cm), tassel size (cm), and ear length (cm). Chi square tests were used to determine the effects of treatments upon the proportion of plants that developed fertile tassel and ear sectors. The ratios of untreated plants with fertile sectors were used to estimate the significance of the ratio of treated plants with fertile sectors.

The numbers of fertile sectors, anthers and kernels were not normally distributed because of the high ratio of non-fertile tassels or ears and variable sizes of the sectors. Nonparametric tests were performed to compare the distributions. The primary test was the Kruskal-Wallis test. In the initial tests, the null hypothesis considered was that the distributions would be the same for each treatment and control. If the null hypothesis was rejected ($P<0.05$), then pair wise comparisons of each treatment to the control using Dunn's method were conducted. The tassel branch number was low incidence count data and was analyzed using the same nonparametric tests mentioned above.

Treated plants were shorter and had smaller tassels with fewer tassel branches compared to the controls (Table 1). The reduction in tassel branch number was especially conspicuous with the B55 haploids treated at the 5–7 leaf stages. The plant height was reduced at the 8 leaf stage and the tassel size was reduced at the 7–8 leaf stages. Some B55 haploids in the control were infected with root rot during mid-growth and this resulted in reduced plant height and ear length. Oh43 haploids experienced plant height reduction from treatments at all stages, tassel size reduction from treatments at the 6–8 leaf stage, and tassel branch number reduction from treatments at 3–5 leaf stage.

Significant increases in the occurrence of fertile sectors on tassels and ears were observed for B55. B55 haploids treated at the 4–8 leaf stage showed a significant increase in the ratio of plants with fertile sectors, the number of fertile sectors on a plant, the number of anthers per tassel, and the number of the kernels produced (Table 2, FIG. 2). The maximum number of anthers in B55 was produced on the 6 leaf stage treatment plants with an average of 521 anthers/tassel (range 36–1178). In contrast, only 2.2 anthers/tassel were produced in the control.

In Oh43 haploids, only the tassels showed a significant increase of fertile sectors. These increases were observed on the plants with the 5–8 leaf stage treatments. With the 6 leaf stage treatment, all plants treated produced anthers (5.3 anthers/plant in average, range 1–16). Even so, the 5 leaf stage treatment produced the maximum number of anthers (19.7 in average, range 0–146). Only 0.2 anther yielded no significant increases of fertility.

The stage-specific effects of nitrous oxide gas to induce fertile sectors in the reproductive organs of treated haploids were demonstrated. Treatment of maize Oh43 haploids at the 3–4 leaf stage had no effect for increasing the fertile sectors on either tassels and ears. Oh43 haploids treated at the 5–8 leaf stage had a significant increase in the number of fertile tassel sectors. The 6 leaf stage appeared to be best for doubling haploids because of the higher ratio (100%) of fertile tassels relative to other treatment stages. Nitrous oxide gas treated B55 haploids produced a larger number of anthers (35.6–521/tassel 3–8 leaf stage treatments) than Oh43 counterparts (0–19.7/tassel 3–8 leaf stage treatments). Also the number of kernels on the ears (10.9–49.0) was greater than those of Oh43 (0.5–18.6). Further, B55 haploids responded to the nitrous oxide gas treatment and produced fertile sectors even at the 3 leaf stage. For B55 haploids, the 5–7 leaf stages appear to be better for seed production by selfing because of the significantly higher frequency of fertile sectors on the tassels (100%), larger number of anthers on the tassels (140–521/tassel), and larger number of kernels on the ears (40.4–47.5/ear).

The difference between B55 and Oh43 haploids illustrated the existence of a genotypic effect on the response to nitrous oxide gas treatment. However, the fact that both B55 and Oh43 responded to nitrous oxide gas and exhibited a significant increase of fertility at the 5 to 7 leaf stage treatments indicated the broad applicability of the technique. These same plants experienced significant reductions in tassel branch number and tassel size (Table 1). These phenomena indicate that the shoot meristems of plants at the 5–7 leaf stages are undergoing tassel branch differentiation. The ineffectiveness of the 3–4 leaf stage treatments may indicate that cells destined for tassel branches or glumes are not yet mitotically active. In the dormant maize embryo, the tassel and ear are each determined by only 2–4 cells (Coe and Neuffer 1978; Poethig et al. 1990). This suggests that further proliferation of these cells is delayed until after the 4 leaf stage. An alternative explanation is that the cells affected by nitrous oxide at 3–4 leaf stage are eliminated during development by cell competition. The significant reduction in tassel branch number at the 5 leaf stage suggests that the cells destined to form tassel branches failed to proliferate as a result of the nitrous oxide gas treatment. Prevent this failure of proliferation may be possible to by shortening the period of the treatment.

Example 4

Doubled Haploid Production Trial on Haploids of Eight Different Origins

Based on the initial results, treatments at the 5–7 leaf stages were selected for further testing. In order to identify the best stage, and to examine the potential for doubled haploid production by the nitrous oxide gas treatment, haploids of eight different origins (induced from the four inbreds, A619, B55, B73, and Oh43, and the four hybrids, B55×A619, B73 R1-scm2×A619 R1-scm2, Oh43×Mol7 and W22×W23,) were treated with nitrous oxide gas (600 kPa+ kPa+100 kPa air, 2 days, room temperature) at the 5, 6 or 7 leaf stage. Ten to nineteen plants were treated for each plot. Self pollinations were conducted on these treated haploids if there were fertile sectors on the tassel. Pollen grains were collected carefully on a sheet of paper and transferred to the silks repeatedly. Silks and husks were cut back prior to pollination in order to permit maximum seed set. The numbers of fertile tassel and ear sectors, as well as the numbers of anthers and selfed kernels were recorded. Statistical analyses were as described above.

The combined data (Table 3, total/average) indicated that the nitrous oxide gas treatment has a positive effect on all the fertility related traits examined. The 6 leaf stage treatment gave the maximum number of doubled haploid progenies (44%, 39 out of 90). This treatment also gave the highest number of anthers (74.3/tassel). In the control, 11% of the plants gave doubled haploid progenies. The data of the haploids derived from B55 and B55×A619 were exempted from the total/average, the ratio of the haploids with anthers (56–74%, 5–7 leaf stage), the number of fertile sectors on the tassels, the number of fertile anthers, and the ratio of haploids with selfed kernels (selfing rate 32–35%, 5 and 6 leaf stage). Figures for the treated plots were significantly higher (P<0.01) than the control.

Of the 8 individual haploid lines, 5 exhibited a significant increase of fertility on the reproductive organs. Haploids derived from B55 produced the highest number of fertile anthers and kernels. Further, all the B55 haploid plants treated at the 6 leaf stage produced anthers (380 in average, range 115–747) and 90% of the plants produced selfed kernels (FIG. 3, 61.6 kernels/ear in average, range 0–104). The haploids derived from B55×A619 also produced a significantly greater number of fertile anthers and more plants with selfed kernels than the controls. The haploids induced from Oh43, A619×B73, and Oh43×Mol7 also responded to nitrous oxide gas treatment and about 30% of the treated haploids produced double haploid progenies after self pollination. However, the number of kernels on the selfed progenies were fewer than that of B55 haploids treated with nitrous oxide.

There was no significant effect of nitrous oxide gas treatment on fertility of the haploids derived from A619, B73 and W22×W23. The ratio of untreated plants with fertile anthers in W22×W23 haploids (55%) was significantly higher (P<0.05 or 0.01) than all lines except B55 and Oh43. The number of spontaneous fertile sectors and anthers on the tassel of W22×W23 haploids was significantly higher than for A619×B73 and B55×A619 haploids (P<0.01, Table 3). W22×W23 and B73 haploids showed higher successful doubled haploid recovery rates (22–32%) without treatment, whereas other lines show only 4–8% succesful doubled haploid recovery rates. The successful selfing rates were not significantly different among the lines tested. B73 haploids treated at the 7 leaf stage had deformed ears and delayed silk emergence, as a result self pollinations were difficult.

There are three types of responses to nitrous oxide gas treatment, which are characterized by the haploids of B55, Oh43, and W22×W23 (Table 3). The B55 haploids responded well to nitrous oxide gas and produced the largest number of anthers and kernels after the treatment. Self pollination became feasible only after nitrous oxide treatment and the successful self pollination rate was very high (90–100%). Data from haploids derived from A619×B55 indicated that responsiveness of B55 was heritable. The Oh43 haploids responded less well to nitrous oxide gas, but still experienced a significant increase of fertile sectors. The self pollination success rates were improved after treatment (20–30%), but the rate was much lower than for B55. The Oh43×Mol7 and A619 haploids behaved similarly. A619 shares 75% genetic constitution with Oh43 (Gerdes and Tracy 1993). The W22×W23 haploids had the highest spontaneous chromosome doubling rate on the male side. A high rate of self pollination was possible without nitrous oxide gas treatment, so the effect of treatment was not clear. The haploids of B73 behaved similarly. A high occurrence of fertile sectors due to spontaneous chromosome doubling has been reported among 282 haploids both on tassels and ears with a successful selfing rate of 12% (Chase, 1952a). This frequency is very close to the successful selfing rate of the combined untreated controls (11%) reported here (Table 3). A genotype that had a high occurrence of fertile sectors on ears has also been reported (Chalyk, 1994). Although there seems to be tendency toward spontaneous chromosome doubling on maize haploid seedlings; the rate is not sufficient for reliable production of doubled haploids.

The results revealed the effectiveness of nitrous oxide gas treatment at the flower primordia formation stage to induce fertile sectors on the reproductive organs of haploids. This technique may also be used for other monocots such as rice, onion, etc. In these species, colchicine treatment at the seedling stage is difficult or ineffective. This procedure may be used to restore fertility of interspecific hybrids.

TABLE 1

Effects of the nitrous oxide gas treatment (600 kPa, 2 days treatment, 3–8 leaf stages) on the growth of maize B55 and Oh43 haploid seedlings.

| Origin of haploids | Stage of the treatment | No. of plants | | Plant height (cm) | | Tassel size (cm) | | No. of tassel branch | | Ear length (cm) |
|---|---|---|---|---|---|---|---|---|---|---|
| Range | (leaf number) | Treated | Survived | Average[1] | Range | Average[1] | Range | Average[2] | Range | Average[1] |
| B55 | 3 | 10 | 9 | 183 d | (161–204) | 29.4 c | (25–34) | 18.8* | (16–22) | 13.9 c (8–21) |
| | 4 | 11 | 11 | 168 bc | (133–213) | 28.7 c | (24–36) | 20.1 | (12–26) | 12.4 b (9–15) |
| | 5 | 9 | 9 | 170 c | (139–195) | 27.8 c | (24–32) | 13.9** | (9–18) | 12.2 b (9–15) |
| | 6 | 10 | 10 | 165 bc | (130–197) | 28.7 c | (24–35) | 14.5** | (7–23) | 12.0 b (4–21) |
| | 7 | 11 | 11 | 168 bc | (136–208) | 26.5 b | (21–34) | 14.3** | (9–20) | 11.3 b (6–20) |
| | 8 | 12 | 12 | 137 a | (114–174) | 23.8 a | (19–34) | 20.4* | (15–31) | 8.8 a (3–14) |
| | Control | | 18 | 161 b | (118–194) | 28.7 c | (24–40) | 25.8 | (18–37) | 9.4 a (4–14) |

TABLE 1-continued

Effects of the nitrous oxide gas treatment (600 kPa, 2 days treatment, 3–8 leaf stages) on the growth of maize B55 and Oh43 haploid seedlings.

| Origin of haploids | Stage of the treatment | No. of plants | | Plant height (cm) | | Tassel size (cm) | | No. of tassel branch | | Ear length (cm) |
|---|---|---|---|---|---|---|---|---|---|---|
| Range | (leaf number) | Treated | Survived | Average[1] | Range | Average[1] | Range | Average[2] | Range | Average[1] |
| Significance | | | | $P < 0.01$ | | $P < 0.05$ | | $P < 0.01$ | | $P < 0.01$ |
| Oh43 | 3 | 12 | 12 | 106 a | (87–154) | 20.6 b | (17–24) | 3.8** | (3–7) | 8.3 a (3–12) |
| | 4 | 13 | 13 | 121 b | (94–146) | 20.5 b | (15–25) | 4.4** | (0–7) | 9.6 b (5–11) |
| | 5 | 14 | 13 | 124 b | (86–165) | 20.6 b | (14–27) | 2.9** | (0–7) | 9.5 b (8–12) |
| | 6 | 16 | 12 | 119 b | (88–150) | 15.1 a | (11–21) | 5.7 | (3–7) | 10.3 c (8–12) |
| | 7 | 16 | 13 | 122 b | (87–144) | 15.5 a | (7–21) | 5.0* | (2–9) | 10.1 b (4–11) |
| | 8 | 16 | 13 | 122 b | (77–143) | 14.5 a | (11–23) | 5.3* | (1–9) | 9.2 b (7–12) |
| | Control | | 22 | 151 c | (116–170) | 21.5 b | (16–27) | 7.3 | (2–14) | 10.3 c (7–12) |
| Significance | | | | $P < 0.01$ | | $P < 0.01$ | | $P < 0.01$ | | $P < 0.05$ |

[1]After examination of analyses of variance, Duncan's Multiple Range tests were conducted. Numbers of same letter are not significantly different.
[2]*, ** - Significant at $P = 0.05$ and $P = 0.01$ respectively from each control. Significance was estimated from nonparametric tests.

TABLE 2

Occurrence of fertile sectors on maize B55 and Oh43 haploids after nitrous oxide gas treatment (600 kPa, 2 days treatment) at various leaf stages (3–8 leaf stages).

| | | | Tassel | | | | Ear (open pollinated) | | |
|---|---|---|---|---|---|---|---|---|---|
| Origin of haploids | Stage of the treatment (leaf number) | No. of plants Examined | Plants with fertile sectors No. | %[1] | No. of fertile sectors /tassel[2] | No. of fertile anthers extruded /tassel[2] | Plants with fertile sectors No. | %[1] | No. of fertile sectors /ear[2] | No. of kernels produced /ear[2] |
| B55 | 3 | 9 | 6 | 67 | 1.1 | 35.6 | 6 | 67 | 1.1 | 49.0* |
| | 4 | 11 | 7 | 64 | 1.5 | 111.5* | 11 | 100** | 2.8** | 21.5** |
| | 5 | 9 | 9 | 100** | 3.0* | 139.6** | 8 | 89* | 1.6 | 40.4** |
| | 6 | 10 | 10 | 100** | 5.7** | 521.1** | 9 | 90* | 1.7 | 45.5** |
| | 7 | 11 | 11 | 100** | 9.6** | 267.3** | 9 | 82 | 1.8 | 47.5** |
| | 8 | 12 | 12 | 100** | >18.6** | 283.2** | 11 | 92** | 2.3** | 10.9* |
| | Control | 18 | 6 | 33 | 0.5 | 2.2 | 9 | 50 | 1.0 | 1.0 |
| Significance | | | | $P < 0.01$ | $P < 0.01$ | $P < 0.01$ | | $P < 0.05$ | $P < 0.05$ | $P < 0.01$ |
| Oh43 | 3 | 12 | 0 | 0 | 0.0 | 0.0 | 4 | 33 | 0.7 | 0.5 |
| | 4 | 13 | 3 | 23 | 0.3 | 1.5 | 6 | 46 | 0.8 | 0.8 |
| | 5 | 13 | 7 | 54** | 1.2* | 19.7** | 6 | 46 | 1.4 | 1.8 |
| | 6 | 12 | 12 | 100** | 1.8** | 5.3** | 8 | 67 | 1.5 | 18.6 |
| | 7 | 13 | 9 | 69** | 2.1** | 5.8** | 6 | 46 | 0.8 | 1.1 |
| | 8 | 13 | 9 | 69** | 1.4** | 3.1** | 6 | 46 | 1.0 | 4.1 |
| | Control | 22 | 3 | 14 | 0.2 | 0.2 | 12 | 55 | 1.0 | 1.0 |
| Significance | | | | $P < 0.01$ | $P < 0.01$ | $P < 0.01$ | | n.s. | n.s. | n.s. |

[1]*, ** - Significant at $P = 0.05$ and $P = 0.01$ respectively from each control accroding to chi-square tests.
[2]*, ** - Significant at $P = 0.05$ and $P = 0.01$ respectively from each control, probabilities were estimated from nonparametric tests.
Note:
n.s. - not significant.

TABLE 3

Occurrence of fertile sectors after nitrous oxide gas treatments (600 kPa, 2 days treatment, 5, 6 and 7 leaf stages) and production of doubled haploids on various origin of maize haploid seedlings.

| | | | | Tassel | | | | Ear | |
|---|---|---|---|---|---|---|---|---|---|
| Origin of haploids | Stage of the treatment (leaf number) | No. of plants Treated | Survived | Plants with fertile sectors No. | %[1] | No. of fertile sectors/ tassel[2] | No. of fertile anthers extruded/ tassel[2] | Plants with kernels after selfing No. | %[1] | No. of kernels produced/ ear[2] |
| A619 | 5 | 12 | 12 | 3 | 25 n.s. | 0.3 n.s. | 4.5 n.s | 2 | 17 n.s. | 0.3 n.s. |
| | 6 | 9 | 9 | 5 | 56 | 0.6 | 3.2 | 3 | 33 | 2.0 |
| | 7 | 14 | 13 | 7 | 54 | 1.6 | 8.2 | 4 | 31 | 1.6 |
| | Control | | 12 | 4 | 33 | 0.3 | 3.6 | 1 | 8 | 0.1 |

TABLE 3-continued

Occurrence of fertile sectors after nitrous oxide gas treatments (600 kPa, 2 days treatment, 5, 6 and 7 leaf stages) and production of doubled haploids on various origin of maize haploid seedlings.

| Origin of haploids | Stage of the treatment (leaf number) | No. of plants Treated | No. of plants Survived | Tassel Plants with fertile sectors No. | Tassel Plants with fertile sectors %[1] | Tassel No. of fertile sectors/ tassel[2] | Tassel No. of fertile anthers extruded/ tassel[2] | Ear Plants with kernels after selfing No. | Ear Plants with kernels after selfing %[1] | Ear No. of kernels produced/ ear[2] |
|---|---|---|---|---|---|---|---|---|---|---|
| B55 | 5 | 10 | 10 | 9 | 90** | 1.6 | 161.3** | 6 | 60** | 31.5* |
|  | 6 | 10 | 10 | 10 | 100** | 4.5** | 380.1** | 9 | 90** | 61.6* |
|  | 7 | 9 | 9 | 9 | 100** | 10.6** | 401.3** | 7 | 78** | 65.6** |
|  | Control |  | 17 | 8 | 47 | 0.6 | 3.9 | 1 | 6 | 0.1 |
| B73 | 5 | 11 | 11 | 5 | 45 n.s. | 0.5 n.s. | 3.5 n.s | 4 | 36 n.s. | 2.4 n.s. |
|  | 6 | 11 | 11 | 7 | 64 | 1.0 | 13.2 | 5 | 45 | 10.7 |
|  | 7 | 11 | 11 | 7 | 64 | 1.4 | 14.9 | 2 | 18 | 0.9 |
|  | Control |  | 18 | 5 | 28 | 0.4 | 2.5 | 4 | 22 | 6.2 |
| Oh43 | 5 | 19 | 14 | 8 | 57 | 0.8 | 11.2* | 4 | 29 n.s | 0.6 n.s. |
|  | 6 | 16 | 12 | 11 | 92** | 1.3** | 5.7** | 2 | 17 | 1.0 |
|  | 7 | 15 | 10 | 7 | 70* | 1.0 | 2.6 | 1 | 10 | 0.1 |
|  | Control |  | 25 | 9 | 36 | 0.4 | 2.8 | 1 | 4 | 0.0 |
| A619 × B73 | 5 | 12 | 11 | 8 | 73** | 1.0* | 20.8** | 4 | 36 n.s. | 4.2 n.s. |
|  | 6 | 11 | 11 | 8 | 73** | 1.7** | 34.5** | 4 | 36 | 6.2 |
|  | 7 | 12 | 12 | 9 | 75** | 1.3** | 4.8* | 2 | 17 | 3.5 |
|  | Control |  | 22 | 2 | 9 | 0.1 | 0.4 | 1 | 5 | 0.1 |
| B55 × A619 | 5 | 15 | 15 | 10 | 67** | 1.1* | 25.7** | 5 | 33 | 1.3 |
|  | 6 | 14 | 14 | 10 | 71** | 3.1** | 109.9** | 7 | 50** | 9.5* |
|  | 7 | 13 | 13 | 12 | 92** | 3.9** | 60.2** | 8 | 62** | 15.7** |
|  | Control |  | 29 | 4 | 14 | 0.1 | 0.3 | 2 | 7 | 0.5 |
| Oh43 × Mo17 | 5 | 11 | 11 | 8 | 73** | 1.0 | 4.2 | 3 | 27 n.s. | 0.5 n.s. |
|  | 6 | 14 | 13 | 13 | 100** | 2.5** | 29.8** | 5 | 38 | 3.8 |
|  | 7 | 19 | 15 | 11 | 73** | 1.8** | 8.3* | 2 | 13 | 0.6 |
|  | Control |  | 25 | 5 | 20 | 0.4 | 4.7 | 2 | 8 | 1.7 |
| W22 × W23 | 5 | 12 | 11 | 7 | 64 n.s. | 1.1 n.s. | 27.6 n.s | 5 | 45 n.s. | 9.5 n.s. |
|  | 6 | 12 | 10 | 6 | 60 | 2.1 | 18.0 | 4 | 40 | 3.3 |
|  | 7 | 8 | 7 | 5 | 71 | 1.9 | 7.1 | 3 | 43 | 11.4 |
|  | Control |  | 22 | 12 | 55 | 1.0 | 37.0 | 7 | 32 | 6.7 |
| Total/Average | 5 | 102 | 95 | 58 | 61** | 0.9** | 32.3** | 33 | 36** | 4.4** |
|  | 6 | 97 | 90 | 70 | 78** | 2.1** | 74.3** | 39 | 44** | 8.6** |
|  | 7 | 101 | 90 | 67 | 74** | 2.8** | 63.5** | 29 | 34** | 7.0** |
|  | Control |  | 170 | 48 | 28 | 0.4 | 6.9 | 19 | 11 | 1.2 |

[1] *, ** - Significant at P = 0.05 and P = 0.01, respectively, from each control accroding to chi-square tests.
[2] *, ** - Significant at P = 0.05 and P = 0.01, respectively, from each control. Probabilities were estimated from nonparametric tests.
Note: n.s. - not significant All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aguiar-Perecin, M. L. R. de and Vosa, C. G. 1985. C-banding in maize. II. Identification of somatic chromosomes. Heredity 54:37–42.

Albertsen M. C. and R. L. Phillips 1981. Developmental cytology of 13 genetic male sterile loci in maize. Can. J. Cytol. 23:195–208.

Alemanno, L., and E. Guiderdoni, 1994: Increased doubled haploid plant regeneration from rice (Oryza sativa L.) anthers cultured on colchicine-supplemented media. Plant Cell Rep. 13, 432–436.

Alexander, D. E. 1957. The genetic induction of autotetraploidy: A proposal for its use in corn breeding. Agron J 49:40–43

Aman, M. A. and K. R. Sarkar 1978. Selection for haploidy inducing potential in maize. Indian J Genet Plant Breed 38:452–457.

Anamthawat-J-nsson, K., S. K. Bdvarsd-ttir, and B. T. Bragason, 1997: Wide hybridization between wheat (Triticum L.) and lymegrass (Leymus Hochst.). Euphytica 93, 293–300.

Anonymous 1975. Primary study on induction of pollen plants of Zea mays. Acta Genet. Sin. 2:143.

Barloy, D., L. Denis and M. Beckert 1989. Comparison of the aptitude for anther culture in some androgenetic doubled haploid maize lines. Maydica 34:303–308.

Berdahl, J. D., and R. E. Barker, 1991: Characterization of autotetraploid Russian wildrye produced with nitrous oxide. Crop Sci. 31, 1153–1155.

Birchler, J. A. 1991. Chromosome manipulations in maize. Chromosome Engineering in Plants: Genetics, Breeding, Evolution. Gupta, P. K. and Tsuchiya, T. (eds). 1991. Elsevier Science Publishers, New York pp.531–559

Birchler, J. A. 1993. Dosage analysis of maize endosperm development. Annu. Rev. Genet. 27:181–204.

Birchler, J. A. 1994a. Heterofertilization. The Maize Handbook. Freeling, M. and Walbot, V., ed. Springer-Verlag. New York. pp. 514–516.

Birchler, J. A. 1994b. Production of a ploidy series. The Maize Handbook. Freeling, M. and Walbot, V., ed. Springer-Verlag. New York. pp. 394–395.

Birchler, J. A. 1994c. Dosage analysis using B-A translocations. The Maize Handbook. Freeling, M. and Walbot, V., ed. Springer-Verlag. New York. pp. 328–329.

Birchler, J A and D. M. Levin 1991. Directed synthesis of a segmental chromosomal transposition—an approach to the study of chromosomes lethal to the gametophyte generation of maize. Genetics 127:609–618.

Bordes, J., R. D. de Vaulx, A. Lapierre, and M. Pollacsek, 1997: Haplodiploidization of maize (Zea mays L.) through induced gynogenesis assisted by glossy markers and its use in breeding. Agronomie 17,291–297.

BŸter, B., 1997: In vitro haploid production in maize. In: S. M. Jain, S. K. Sopory, and R. E. E. Veilleux (eds.), In vitro haploid production in higher plants, 37–71. Kluwer Academic Publishers, Dordrecht, The Netherlands.

Carvalho, C. R. de and Saraiva, L. S. 1993. An air drying technique for maize chromosomes without enzymatic maceration. Biotech. Histochem. 68:142–145.

Chalyk, S. T., 1994: Properties of maternal haploid maize plants and potential application to maize breeding. Euphytica 79,13–18.

Chalyk, S. T., 2000: Obtaining fertile pollen in maize maternal haploids. Maize Genet. Coop. Newslett. 74,17–18, (www.agron.missouri.edu/mnl/74/93chalyk.html).

Chandler, V. 1994 Overview of cloning genes using transposon tagging. The Maize Handbook. Freeling, M. and Walbot, V., ed. Springer-Verlag. New York. pp. 647–652.

Chang, M. T. and M. G. Neuffer 1989a. Maize microsporogenesis. Genome 32:232–244

Chang, M. T. and M. G. Neuffer 1989b. A simple method for staining nuclei of mature and germinated maize pollen. Stain Technol. 64:181–184.

Chase, S. S. 1949. Monoploid frequencies in a commercial double cross hybrid maize, and in its component single cross hybrids and inbred lines. Genetics 34: 328–332.

Chase, S. S. 1952. Production of homozygous diploids of maize from monoploids. Agron J 44 263–267.

Chase, S. S. 1969. Monoploids and monoploid-derivatives of maize (Zea mays L.). Bot. Rev. 35:117–167.

Chase, S. S., 1952a: Monoploids in maize. In: J. W. Gowen (ed.) Heterosis, 390–399. Iowa State College Press, Ames Iowa.

Chase, S. S., 1952b: Production of homozygous diploids of maize from monoploids. Agron. J. 44, 263–267.

Chase, S. S., 1969: Monoploids and monoploid-derivatives of maize (Zea mays L.). Bot. Rev. 35, 117–167.

Chen, C. C. 1969. The somatic chromosomes of maize. Can. J. Genet. Cytol. 11:752–754.

Chen, Y. C. S. and S. McCormick 1996. Sidecar pollen, an Arabidopsis thaliana male gametophytic mutant with aberrant cell divisions during pollen development. Development 122: 3243–3253.

Chomet, P. S. 1994. Transposon tagging with mutator. The Maize Handbook. Freeling, M. and Walbot, V., ed. Springer-Verlag. New York. pp. 244–248.

Coe, E. H. 1959. A line of maize with high haploid frequency. Am Nat 93:381–382.

Coe, E. H. and K. R. Sarkar 1964. The detection of haploids in maize. J Hered 55:231–233.

Coe, E. H. Jr., and M. G. Neuffer, 1978: Embryo cells and their destinies in the corn plant. In: S. Subtelny and I. M. Sussex, (eds.), The Clonal Basis of Development, 113–129. Academic Press, New York.

Coe, E. H., S. McCormick and S. A. Modena 1981. White pollen in maize. J. Hered. 72:318–320

Dieu, P. and M. Beckert 1986. Further studies of androgenetic embryo production and plant regeneration from in vitro cultured anthers in maize (Zea mays L.). Maydica 31:245–259.

Dolezel, J., Cihalikova, J., and Lucretti, S. 1992. A high-yield procedure for isolation of metaphase chromosomes from root tips of Vicia faba L. Planta 188:93–98.

Dolezel, J., Lucretti, S. and Schubert, I. 1994. Plant chromosome analysis and sorting by flow cytometry. Critical Reviews in Plant Sciences 13:275–309.

Dumas, C. and H. L. Mogensen 1993. Gametes and fertilization: Maize as a model system for experimental embryogenesis in flowering plants. Plant Cell 5:1337–1348.

Dvorak, J., and B. L. Harvey, 1973: Production of aneuploids in Avena sativa L. by nitrous oxide. Can. J. Genet. Cytol. 15, 649–651.

Dvorak, J., B. L. Harvey, and B. E. Coulman, 1973: The use of nitrous oxide for producing eupolyploids and aneuploids in wheat and barley. Can. J. Genet. Cytol. 15, 205–214.

Eder, J., and S. Chalyk, 2002: In vivo haploid induction in maize. Theor. Appl. Genet. 104, 703–708.

Furusho, M., T. Baba, O. Yamagaguchi, T. Yoshida, Y. Hamachi, R. Yoshikawa, K. Mizuta, and M. Yoshino, 1999: Breeding of a new malting barley cultivar Houshun by the bulbosum method. Breeding Sci. 49, 281–284.

Gayen, P., J. K. Madan, R. Kumar, and K. R. Sarkar, 1994: Chromosome doubling in haploids through colchicine. Maize Genet. Coop. Newslett. 68, 65, (www.agron.missouri.edu/mnl/68/101 gayen.html).

Genovesi, A. D. and G. B. Collins 1982. In vitro production of haploid plants of corn via anther culture. Crop Sci. 22:1137–1144.

Gerdes, J. T., and W. F. Tracy, 1993: Pedigree diversity within the Lancaster Surecrop haterotic group of maize. Crop Sci. 33,334–337.

Goodsell, S. F. 1961. Male sterility in corn by androgenesis. Crop Sci 1:227–228

Greenblatt, I. M., and M. Bock, 1967: A commercially desirable procedure for detection of monoploids in maize. J. Hered. 58, 9–13.

Guenov, M. 1991. Producing mitotic maize autotetraploids by colchicine treatment. Genetica i Selektsiya 23:430–439

Guo, M. and Birchler, J. A. 1994. Trans-acting dosage effects on the expression of model gene systems in maize aneuploids. Science 266:1999–2002.

Guo, M., D. Davis and J. A. Birchler 1996. Dosage effects on gene expression in a maize ploidy series. Genetics 142:1349–1355.

Hadlaczky, G Y. and Kálmán, L. 1975. Discrimination of homologous chromosomes of maize with giemsa staining Heredity 35:371–374.

Hansen, A. L., A. Gertz, M. Joersbo, and S. B. Andersen, 1995: Short-duration colchicine treatment for in vitro chromosome doubling during ovule culture of *Beta vulgaris* L. Plant Breeding. 114, 515–519.

Hansen, A. L., A. Gertz, M. Joersbo, and S. B. Andersen, 1998: Antimicrotubule herbicides for in vitro chromosome doubling in *Beta vulgaris* L. ovule culture. Euphytica 101, 231–237.

Hansen, F. L., S. B. Andersen, I. K. Due, and A. Olesen, 1988: Nitrous oxide as a possible alternative agent for chromosome doubling of wheat haploids. Plant Sci. 54, 219–222.

Hansen, N. J. P., and S. B. Andersen, 1996: In vitro chromosome doubling potential of colchicine, oryzalin, trifluralin, and APM in *Brassica napus* microspore culture. Euphytica 88, 159–164.

Hansen, N. J. P., and S. B. Andersen, 1998: In vitro chromosome doubling with colchicine during microspore culture in wheat (*Triticum aestivum* L.). Euphytica 102, 101–108.

Hassawi, D. S., and G. H. Liang 1991: Antimitotic agents: Effects on double haploid production in wheat. Crop Sci. 31, 723–726.

Hormaza, J. I., and M. Herrero. 1992. Pollen selection. Review. Theor. Appl. Genet. 83:663–672.

Jamieson, G., Evans, I. J. and Barnes, S. R. 1986. An enzymatic method of preparing plant chromosomes for in situ hybridization. Stain Technol. 61:21–25.

Jewell, D. C. and Islam-Faridi, N. 1994. A technique for somatic chromosome preparation and C-banding of maize. In: The Maize Handbook. Freeling, M. and Walbot, V., Ed. Springer-Verlag. New York. pp. 484–493.

Kato A. 1999a. Air drying method using nitrous oxide for chromosome counting in maize. Biotechnic & Histochemistry 74:160–166.

Kato A. 1999b. Induction of bicellular pollen by trifluralin treatment and occurrence of triploids and aneuploids after fertilization in maize. Genome 42:154–157.

Kato A. 1999c. Single fertilization in maize. Journal of Heredity 90:276–280.

Kato, A. 1990. Heterofertilization exhibited by using highly haploid inducing line "Stock 6" and supplementary cross. Maize Genet Coop Newslett 64:109–110.

Kato, A. 1992. Detection of an unfertilized polar nucleus with a fertilized egg cell. Maize Genet Coop Newslett 66:105–106.

Kato, A. 1996. Induction of bicellular pollen and dihaploidization of tetraploid maize. Maize Genet Coop Newslett 70:25–26

Kato, A. 1997a. Nitrous oxide ($N_2O$) is effective in chromosome doubling of maize seedlings. Maize Genet. Coop. Newslett. 71:36–37. (www.agron. missouri.edu/mnl.html).

Kato, A. 1997b. An improved method for chromosome counting in maize. Biotech. Histochem. 72:249–252

Kato, A. 1997c. Induced single fertilization in maize. Sex Plant Reprod 10:96–100.

Kato, A. 1998. Nitrous oxide ($N_2O$) is effective for chromosome counting in maize. Maize Genet Coop Newslett 72:32–33

Kato, A. 1998a. Hematoxylin procedure for staining mature pollen grains in maize with dimethylsulfoxide as a clearing agent. Biotech Histochem 73:1–5.

Katsiotis, A., R. E. Hanneman Jr, and R. A. Forsberg, 1995: Endosperm balance number and the polar-nuclei activation hypotheses for endosperm development in interspecific crosses of Solanaceae and Gramineae, respectively. Theor. Appl. Genet. 91, 848–855.

Kermicle, J. L. 1969. Androgenesis conditioned by a mutation in maize. Science 166:1422–1424

Kermicle, J. L. 1971. Pleiotropic effects on seed development of the indeterminate gametophyte gene in maize. Amer J Bot 58:1–7

Kiesselbach, T. A. (1949) The structure and reproduction of corn. Cold spring harbor laboratory press. pp. 18.

Kihara, H., and K. Tsunewaki, 1960: Production of polyploid wheat by nitrous oxide. Proc. Jap. Acad. 36, 658–663.

Kindiger, B. 1994. A technique for the preparation of somatic chromosomes of maize. In: The Maize Handbook. Freeling, M. and Walbot, V., Ed. Springer-Verlag. New York. pp. 481–483.

Kindiger, B. and J. B. Beckett 1985. A hematoxylin staining procedure for maize pollen grain chromosomes Stain Technol. 60:265–269.

Kindiger, B. and S. Hamann 1993. Generation of haploids in maize: a modification of the indeterminate gametophyte (ig) system. Crop Sci. 33:342–344.

Kindiger, B., J. B. Beckett and E. H. Coe 1991. Differential effects of specific chromosomal deficiencies on the development of the maize pollen grain. Genome 32:579–594.

Kiviharju, E., M. Puolimatka, M. Saastamoinen, and E. Pehu, 2000: Extension of anther culture to several genotypes of cultivated oats. Plant Cell Rep. 19, 674–679.

Ladizinsky, G., 2000: A synthetic hexaploid (2n=42) oat from the cross of *Avena strigosa* (2n=14) and domesticated A. magna (2n=28). Euphytica 116, 231–235.

Lashermes, P., and M. Beckert, 1988: Genetic control of maternal haploidy in maize (*Zea mays* L.) and selection of haploid inducing lines. Theor. Appl. Genet. 76, 405–410.

Lee, J. -H., Arumuganathan, K., Kaeppler, S. M., Kaeppler, H. F. and Papa, C. M. 1996. Cell synchronization and isolation of metaphase chromosomes from maize (*Zea mays* L.) root tips for flow cytometric analysis and sorting. Genome 39:697–703.

Lee, J. -H., Arumuganathan, K., Yen, Y., Kaeppler, S., Kaeppler, H. and Baenziger P. S. 1997. Root tip cell cycle synchronization and metaphase-chromosome isolation suitable for flow sorting in common wheat (*Triticum aestivum* L.). Genome 40:633–638.

Lin, B-Y. 1977. A squash technique for studying the cytology of maize endosperm and other tissues. Stain Technol. 52:197–201.

Lin, B-Y. 1978. Structural modifications of the female gametophyte associated with the indeterminate gametophyte (ig) mutant in maize. Can. J. Genet. Cytol. 20:249–257.

Lin, B-Y. 1982. Association of endosperm reduction with parental imprinting in maize. Genetics 100:475–486.

Loukides, C. A., A. H. Broadwater, and P. A. Bedinger 1995. Two new male-sterile mutants of *Zea mays* (Poaceae) with abnormal tapetal cell morphology. Amer. J. Bot. 82:1017–1023.

Mangelsdorf, P. C. 1932. Mechanical separation of gametes in maize. J. Hered. 23:289–295.

Mascarenhas, J. P. 1990. Gene activity during pollen development. Annu. Rev. Plant Physiol. Plant Mol. Biol. 41:317–338.

McConchie, C. A., T. Hough and R. B. Knox 1987. Ultrastructural analysis of the sperm cells of mature pollen of maize, *Zea mays*. Protoplasma 139:9–19.

McCormick, S. 1993. Male gametophyte development. Plant Cell 5:1265–1275.

Mitchell, J. C. and J. F. Petolino 1991. Plant regeneration from haploid suspension and protoplast cultures from isolated microspores of maize. J. Plant Physiol. 137: 530–536.

Montezuma-de-Carvalho, J. 1967, The effect of $N_2O$ on pollen tube mitosis in styles and its potential significance for inducing haploidy in potato. Euphytica 16:190–198.

Murata, M. 1983. Staining air dried protoplasts for study of plant chromosomes. Stain Technol. 58:101–106.

Murigneux, A., D. Barloy, P. Leroy and M. Beckert 1993. Molecular and morphological evaluation of doubled haploid lines in maize. 1. Homogeneity within DH lines. Theor. Appl. Genet. 86:837–842.

Nanda, D. K., and S. S. Chase, 1966: An embryo marker for detecting monoploids of maize (*Zea mays* L.). Crop Sci. 6, 213–215.

Nelson, O. E. 1994. The gametophyte factors in maize. The Maize Handbook. Freeling, M. and Walbot, V., ed. Springer-Verlag. New York. pp. 496–503.

Neuffer, M. G. 1957 Additional evidence on the effect of x-ray and ultraviolet radiation on mutation in maize. Genetics 42:273–282.

Neuffer, M. G. 1994. Mutagenesis. The Maize Handbook. Freeling, M. and Walbot, V., ed. Springer-Verlag. New York. pp. 212–219

Neuffer, M. G. and E. H. Coe 1978. Paraffin oil technique for treating mature corn pollen with chemical mutagens. Maydica 23:21–28

Neuffer, M. G., E. H. Coe and S. Wessler 1997. Mutants of Maize. Cold Spring Harbor Laboratory Press. 263–266

Notsuka, K., T. Tsuru, and M. Shiraishi, 2000: Induced polyploid grapes via in vitro chromosome doubling. J. Jpn. Soci. Hort. Sci. 69, 543–551.

. . . stergren, G. 1944. Colchicine mitosis, chromosome contraction, narcosis and protein chain folding. Hereditas 30:429–467.

. . . stergren, G. 1954. Polyploids and aneuploids of *Crepis capillaris* produced by treatment with nitrous oxide. Genetica 27:54–64.

. . . stergren, G., 1944: Colchicine mitosis, chromosome contraction, narcosis and protein chain folding. Hereditas 30, 429–467.

Pasakinskiene, I., 2000: Culture of embryos and shoot tips for chromosome doubling in *Lolium perenne* and sterile hybrids between *Lolium* and *Festuca*. Plant Breeding 119, 185–187.

Petolino, J. F. and S. A. Thompson 1987. Genetic analysis of anther culture response in maize. Theor. Appl. Genet. 74:284–286.

Petolino, J. F., A. M. Jones, and S. A. Thompson, 1988: Selection for increased anther culture response in maize. Theor. Appl. Genet. 76, 157–159.

Petolino, J. F., and A. M. Jones, 1986: Anther culture of elite genotypes of maize. Crop Sci. 26, 1072–1074.

Poethig, R. S., C. N. McDaniel, and E. H. Coe, 1990: The cell lineage of the maize shoot. In: Genetics of Pattern Formation and Growth Control, A. Mahowald, (ed.), 197–208. Wiley-Liss, Inc., New York.

Randolph, L. F. 1932. Some effects of high temperature on polyploidy and other variations in maize. Proc. Nat. Acad. Sci. 18:222–229.

Rayburn, A. L. and Gill, B. S. 1985. Use of biotin-labeled probes to map specific DNA sequences on wheat chromosomes. J. Hered. 76:78–81.

Rayburn, A. L. and Gold, J. R. 1982. A procedure for obtaining mitotic chromosomes from maize. Maydica 27:113–121.

Redha, A., T. Attia, B. BŸter, S. Saisingtong, P. Stamp, and J. E. Schmid, 1998: Improved production of doubled haploids by colchicine application to wheat (*Triticum aestivum* L.) anther culture. Plant Cell Rep. 17, 974–979.

Reiffers, I., and A. B. Freire, 1990: Production of doubled haploid rice plants (*Oryza sativa* L.) by anther culture. Plant Cell Tissue Organ Cult. 21, 165–170.

Rhoades, M. M. and E Dempsey 1966. Induction of chromosome doubling at meiosis by the elongate gene in maize. Genetics 54:505–522

Ritchie, S. W., J. J. Hanway, and G. O. Benson, 1997. How a corn plant develops Iowa State University of Science and Technology Cooperative Extension Service, Ames, Iowa. Special Report 48,1–21 (www.maize.agron.iastate.edu/corngrows.html).

Robertson, D. S. 1978. Characterization of a mutator system in maize. Mutat. Res. 51:21–28.

Robertson, D. S., 1984: A study of heterofertilization in diverse lines of maize. J. Hered. 75, 457–462.

Rougier, M., A. F. Antoine, D. Aldon and C. Dumas 1996. New lights in early steps of in vitro fertilization in plants. Sex. Plant Reprod. 9:324–329.

Sachan, J K S. and Tanaka, R. 1977. Variation and pattern of C-banding in *Zea* chromosomes. Nucleus 20:61–64.

Saisingtong, S., J E. Schmid, P. Stamp, and B. BŸter, 1996: Colchicine-mediated chromosome doubling during anther culture of maize (*Zea mays* L.). Theor. Appl. Genet. 92, 1017–1023.

Sallee, P. J. 1982. Prefixation and staining of the somatic chromosomes of corn. In: Maize for Biological Research. Sheridan, W. F. Ed. University Press. University of North Dakota. pp. 119–120.

Sallee, P. J. and Kimber, G. 1981. The use of DMSO in the prefixation of somatic chromosomes. Cereal Res. Comm. 9:199–203.

Sari-Gorla, M. S. Ferrario, M. Villa and M. E. Pe 1996. gaMS-1: a gametophytic male sterile mutant in maize. Sex. Plant Reprod. 9:216–220.

Sari-Gorla, M., E. Gatti, M. Villa and M. E. Pe 1997. A multi-nucleate male-sterile mutant of maize with gametophytic expression. Sex. Plant Reprod. 10:22–26.

Sarkar, K. R. and E. H. Coe 1966. A genetic analysis of the origin of maternal haploids in maize. Genetics 54:453–464.

Sarkar, K. R. and E. H. Coe 1971a. Origin of parthenogenetic diploids in maize and its implications for the production of homozygous lines. Crop Sci 11:543–544.

Sarkar, K. R. and E. H. Coe 1971b. Analysis of events leading to heterofertilization in maize. J Hered 62:118–120.

Sarkar, K. R. and E. H. Coe 1971c. Anomalous fertilization in diploid-tetraploid crosses in maize. Crop Sci 11:539–542.

Sarkar, K. R., and E. H. Coe, 1966: A genetic analysis of the origin of maternal haploids in maize. Genetics 54, 453–464.

Sarkar, K. R., S. Panke, and J. K. S. Sachan, 1972: Development of maternal-haploidy-Inducer lines in maize (*Zea mays* L.). Indian J. Agric. Sci. 42, 781–786.

Schubert, I., Dolezel, J., Houben, A., Scherthan, H. and Wanner, G. 1993. Refined examination of plant metaphase chromosome structure at different levels made feasible by new isolation methods. Chromosomal 02:96–101.

Schwartz, D and J. C. Osterman 1976. A pollen selection system for Alcohol dehydrogenase-negative mutants in plants. Genetics 83:63–65.

Simeone, R., D. Pignone, A. Blanco, and M. Attolico, 1989: Cytology and fertility of hybrids and amphiploids between *Aegilops caudata* L.×*Triticum turgidum* (L.) Thell. Plant Breeding 103, 189–195.

Sprague, G. F. 1932. The nature and extent of hetero-fertilization in maize. Genetics 17:358–368

Stinson, J. R., A. J. Eisenberg, R. P. Willing, M. E. Pe, D. D. Hanson, J. P. Mascarenhas 1987. Genes expressed in the male gametophyte of flowering plants and their isolation. Plant. Physiol. 83:442–447.

Subrahmanyam N. C. and Kasha K. J. 1975. Chromosome doubling of barley haploids by nitrous oxide and colchicine treatment. Can. J. Genet. Cytol. 17:573–583.

Subudhi, P. K., R. P. Borkakati, S. S. Virmani and N. Huang 1997. Molecular mapping of a thermosensitive genetic male sterility gene in rice using bulked segregant analysis. Genome 40: 188–194.

Tanaka, I. 1993. Development of male gametes in flowering plants. J Plant Res 106:55–63

Taylor, N. L., M. K. Anderson, K. H. Quesenberry, and L. Watson, 1976: Doubling the chromosome number of *Trifolium* species using nitrous oxide. Crop Sci. 16, 516–518.

Turcich, M. P., D. A. Hamilton, J. P. Mascarenhas 1993. Isolation and characterization of pollen-specific maize genes with sequence homology to ragweed allergens and pectatelyases. Plant Mol Biol 23: 1061–1065.

Wan, Y. and J. M. Widholm 1993. Anther culture of maize. Plant Breed. Rev. 11:199–224

Wan, Y., D. R. Duncan, A. L. Rayburn, J. F. Petolino and J. M. Widholm 1991. The use of antimicrotubule herbicides for the production of doubled haploid plants from anther-derived maize callus. Theor Appl Genet 81:205–211.

Wan, Y., J. F. Petolino, and J. M. Widholm, 1989: Efficient production of doubled haploid plants through colchicine treatment of anther-derived maize callus. Theor. Appl. Genet. 77, 889–892.

Ward, E. J. 1980. Banding patterns in maize mitotic chromosomes. Can. J. Genet. Cytol. 22:61–67.

Zeilinga, A. E., and H. P. Schouten, 1968: Polyploidy in garden tulips. II. The production of tetraploids. Euphytica 17, 303–310.

What is claimed is:

1. A method of obtaining a plant with a doubled chromosome number comprising:
   a) obtaining a starting maize plant;
   b) treating said plant with a selected pressure of from about 500 kPa to about 700 kPa nitrous oxide gas for from about 24 hours to about 144 hours during the 3 to 8 leaf stage of development of said plant during which formation of the floral primordium takes place, wherein the selected pressure yields doubled sectors within said floral primordium and the plant remains amenable to self pollination;
   c) self pollinating the plant; and
   d) selecting a progeny plant with doubled chromosome number derived from the self pollinating.

2. The method of claim 1, wherein the starting plant is further defined as a haploid plant and the progeny plant is a doubled haploid plant.

3. The method of claim 2, wherein the haploid plant is obtained from a hybrid plant.

4. The method of claim 1, wherein the starting plant is heterozygous.

5. The method of claim 4, wherein the starting plant is a member of a non-uniform population of plants.

6. The method of claim 3, wherein the hybrid plant is an $F_1$ hybrid plant.

7. The method of claim 1, wherein the starting plant is an interspecific hybrid plant.

8. The method of claim 1, wherein the selected pressure is about 600 kPa.

9. The method of claim 1, wherein the treating comprises treating said haploid plant with nitrous oxide for a preselected period of time.

10. The method of claim 1, wherein the preselected period of time is about 24 hours.

11. The method of claim 1, wherein the preselected period of time is about 36 hours.

12. The method of claim 1, wherein the preselected period of time is about 48 hours.

13. The method of claim 1, wherein the preselected period of time is about 60 hours.

14. The method of claim 1, wherein the preselected period of time is about 72 hours.

15. The method of claim 1, wherein the preselected period of time is about 96 hours.

16. The method of claim 1, wherein the preselected period of time is about 120 hours.

17. The method of claim 1, wherein the preselected period of time is about 144 hours.

18. The method of claim 1, wherein the step of treating is repeated at least once.

19. The method of claim 18, wherein treating is repeated twice.

20. The method of claim 18, wherein treating is repeated three times.

21. The method of claim 18, wherein treating is repeated four times.

22. The method of claim 1, wherein treating is carried out at the 4 to 7 leaf stage of development of said plant.

23. The method of claim 1, wherein treating is carried out at the 6 leaf stage of development of said plant.

24. The method of claim 1, wherein the self pollinating comprises allowing said plant to naturally self pollinate.

25. The method of claim 1, wherein the self pollinating comprises manual fertilization of a flower on said plant.

26. The method of claim 1, wherein the starting plant is diploid.

27. The method of claim 1, wherein the starting plant is triploid.

28. The method of claim 1, wherein the starting plant is tetraploid.

29. The method of claim 1, wherein the starting plant is hexaploid.

30. The method of claim 1, wherein the starting plant is octoploid.

31. A method of plant breeding comprising the steps of
   a) crossing at least a first and a second parent maize plant to produce a heterozygous plant comprising a selected genetic background;
   b) producing a haploid progeny plant derived from said hybrid plant;
   c) treating the haploid progeny plant with a selected pressure of from about 500 kPa to about 700 kPa nitrous oxide gas for a preselected period of time from about 24 hours to about 144 hours during the 3 to 8 leaf stage of development of said progeny plant during which formation of the floral primordium takes place, wherein the selected pressure yields doubled sectors within said floral primordium and the progeny plant remains amenable to self pollination;

d) self pollinating the progeny plant; and
e) selecting a doubled haploid progeny plant derived from the self pollinating, wherein the progeny plant has a desired genetic background.

32. The method of claim 31, wherein the selected pressure is about 600 kPa.

33. The method of claim 31, wherein the preselected period of time is about 24 hours.

34. The method of claim 31, wherein the preselected period of time is about 36 hours.

35. The method of claim 31, wherein the preselected period of time is about 48 hours.

36. The method of claim 31, wherein the preselected period of time is about 60 hours.

37. The method of claim 31, wherein the preselected period of time is about 72 hours.

38. The method of claim 31, wherein the preselected period of time is about 96 hours.

39. The method of claim 31, wherein the preselected period of time is about 120 hours.

40. The method of claim 31, wherein the preselected period of time is about 144 hours.

41. The method of claim 31, wherein treating is carried out at the 4 to 7 leaf stage of development of said plant.

42. The method of claim 31, wherein treating is carried out at the 6 leaf stage of development of said plant.

43. The method of claim 31, wherein the self pollinating comprises allowing said plant to naturally self pollinate.

44. The method of claim 31, wherein the self pollinating comprises manual fertilization of a flower on said plant.

* * * * *